(12) United States Patent
Panarello

(10) Patent No.: US 12,329,908 B2
(45) Date of Patent: Jun. 17, 2025

(54) RESPIRATORY APPARATUS WITH MULTIPLE POWER SUPPLIES

(71) Applicant: ResMed Pty Ltd, Bella Vista (AU)

(72) Inventor: Adam Panarello, Sydney (AU)

(73) Assignee: ResMed Pty Ltd (AU)

( * ) Notice: Subject to any disclaimer, the term of this patent is extended or adjusted under 35 U.S.C. 154(b) by 98 days.

(21) Appl. No.: 18/319,592

(22) Filed: May 18, 2023

(65) Prior Publication Data

US 2023/0302243 A1    Sep. 28, 2023

Related U.S. Application Data

(63) Continuation of application No. 16/755,096, filed as application No. PCT/AU2018/051080 on Oct. 8, 2018, now Pat. No. 11,684,735.

(Continued)

(51) Int. Cl.
*A61M 16/00*    (2006.01)
*A61M 16/06*    (2006.01)
(Continued)

(52) U.S. Cl.
CPC ...... *A61M 16/024* (2017.08); *A61M 16/0066* (2013.01); *A61M 16/0633* (2014.02);
(Continued)

(58) Field of Classification Search
CPC .............. A61M 16/00; A61M 16/0057; A61M 16/0066; A61M 16/0069; A61M 16/022;
(Continued)

(56) References Cited

U.S. PATENT DOCUMENTS 6,532,957 B2    3/2003   Berthon-Jones
6,810,876 B2   11/2004   Berthon-Jones
(Continued)

FOREIGN PATENT DOCUMENTS

CN    104271189 A    1/2015
CN    104971416 A   10/2015
(Continued)

OTHER PUBLICATIONS

"How does Qi Wireless Charging work?" Dec. 14, 2018 <http://web.archive.org/web/20140731075916/https://www.qinside.biz/en/support/howdoeswireless-charging-work > Published on Jul. 31, 2014.

(Continued)

*Primary Examiner* — Joseph D. Boecker
(74) *Attorney, Agent, or Firm* — Botos Churchill IP Law LLP

(57) ABSTRACT

A respiratory apparatus includes components to permit different operations of the apparatus with different power supplies. For example, a respiratory therapy apparatus for controlling a respiratory therapy may include a power input circuit to receive a first power or a second power. The first power may be provided by a connectable low-power power supply and the second power by a connectable high-power power supply. A controller of the respiratory apparatus coupled to the power input circuit may be configured to detect one of the power supplies, and based on the detection, selectively activate one of a first mode of operation and a second mode of operation. The first mode of operation may be a non-therapy mode with the first power such as for a data setup or data transfer with the respiratory therapy apparatus and the second mode of operation may be a therapy mode with the second power.

14 Claims, 15 Drawing Sheets

Related U.S. Application Data

(60) Provisional application No. 62/574,019, filed on Oct. 18, 2017.

(51) Int. Cl.
*A61M 16/10* (2006.01)
*A61M 16/16* (2006.01)
*G06F 1/26* (2006.01)

(52) U.S. Cl.
CPC ......... *A61M 16/1075* (2013.01); *G06F 1/263* (2013.01); *A61M 2016/0027* (2013.01); *A61M 2016/0039* (2013.01); *A61M 16/1005* (2014.02); *A61M 16/105* (2013.01); *A61M 16/16* (2013.01); *A61M 2202/0208* (2013.01); *A61M 2205/18* (2013.01); *A61M 2205/3368* (2013.01); *A61M 2205/3576* (2013.01); *A61M 2205/3646* (2013.01); *A61M 2205/502* (2013.01); *A61M 2205/52* (2013.01); *A61M 2205/581* (2013.01); *A61M 2205/582* (2013.01); *A61M 2205/583* (2013.01); *A61M 2205/8212* (2013.01); *A61M 2205/8243* (2013.01); *A61M 2205/8262* (2013.01)

(58) Field of Classification Search
CPC ............ A61M 16/024; A61M 16/1075; A61M 16/16; A61M 2205/50; A61M 2205/52; A61M 2205/8206; A61M 2205/8212; A61M 2205/8243; A61M 2205/8262; G06F 1/263; A62B 18/006; A62B 18/045
See application file for complete search history.

(56) References Cited

U.S. PATENT DOCUMENTS

| | | |
|---|---|---|
| 7,252,088 B1 | 8/2007 | Nieves-Ramirez |
| 7,469,698 B1 | 12/2008 | Childers et al. |
| 8,418,692 B2 | 4/2013 | Sanchez |
| 8,738,952 B1 | 5/2014 | Lachwani et al. |
| 8,844,522 B2 | 9/2014 | Huby et al. |
| 9,713,690 B2 | 7/2017 | Somaiya et al. |
| 11,684,735 B2 * | 6/2023 | Panarello .......... A61M 16/0066 128/204.17 |
| 2007/0163588 A1 * | 7/2007 | Hebrank ........... A61M 16/0069 128/205.29 |
| 2008/0011296 A1 * | 1/2008 | Schatzl .................. A61B 5/087 128/202.22 |
| 2008/0149101 A1 | 6/2008 | Becker et al. |
| 2009/0199855 A1 | 8/2009 | Davenport |
| 2010/0065054 A1 | 3/2010 | Hanson et al. |
| 2010/0101574 A1 | 4/2010 | Bassin |
| 2010/0170513 A1 * | 7/2010 | Bowditch .......... A61M 16/0066 128/204.23 |
| 2010/0300443 A1 | 12/2010 | Becker et al. |
| 2011/0017212 A1 * | 1/2011 | Kenyon ............ A61M 16/0816 122/4 R |
| 2011/0034819 A1 | 2/2011 | Desforges et al. |
| 2011/0084552 A1 | 4/2011 | Faerevaag |
| 2011/0162647 A1 | 7/2011 | Hubby et al. |
| 2011/0203588 A1 | 8/2011 | Armitstead et al. |
| 2011/0259332 A1 | 10/2011 | Sanchez et al. |
| 2012/0029304 A1 | 2/2012 | Medina et al. |
| 2012/0167880 A1 * | 7/2012 | Jacob ................. A61M 16/024 128/203.14 |
| 2014/0318535 A1 | 10/2014 | Bullock et al. |
| 2014/0366876 A1 | 12/2014 | Huby et al. |
| 2015/0120067 A1 | 4/2015 | Wing et al. |
| 2015/0157818 A1 * | 6/2015 | Darby ................... A61M 16/06 128/201.13 |
| 2016/0077562 A1 | 3/2016 | Smith |
| 2016/0193437 A1 | 7/2016 | Bao et al. |
| 2018/0001049 A1 * | 1/2018 | Schuller ............ B01D 53/0415 |
| 2021/0008312 A1 * | 1/2021 | Young ................. G06F 21/6245 |

FOREIGN PATENT DOCUMENTS

| | | |
|---|---|---|
| DE | 102016008335 A1 | 1/2017 |
| JP | 2008047023 A | 2/2008 |
| JP | 2008518640 A | 6/2008 |
| JP | 2015506253 A | 3/2015 |
| JP | 2015085202 A | 5/2015 |
| JP | 2017506962 A | 3/2017 |
| WO | 2004112873 A1 | 12/2004 |
| WO | 2009113060 A2 | 9/2009 |
| WO | 2009113060 A3 | 3/2010 |
| WO | 2010027282 A2 | 3/2010 |
| WO | 2011099965 A1 | 8/2011 |
| WO | 2013056171 A2 | 4/2013 |
| WO | 2014007655 A2 | 1/2014 |
| WO | 2015132682 A1 | 9/2015 |
| WO | 2017213934 A1 | 12/2017 |
| WO | 2018215978 A1 | 11/2018 |

OTHER PUBLICATIONS

First Office Action for Chinese Application No. 2018800755845 dated Mar. 21, 2022.
International Search Report PCT Application No. PCT/AU2018/051080.
Notification of Grant issued in corresponding Chinese Patent Application No. 2018800755845, mailed Apr. 22, 2023, 5 pages.
Office Action for corresponding JP Application No. P2020-521941 dated Jul. 7, 2022 with English Translation (23 pages).
Respironics Trilogy Manual, 2010, Version 5.
Extended European Search Report from corresponding European Application No. 23176017.4 dated Oct. 6, 2023 (9 pp.).
Office Action issued in corresponding Japanese Patent Application No. 2023-030811, mailed Sep. 8, 2023, 7 pages.
First Office Action issued in corresponding Japanese Patent Application No. 2023-030811, mailed Apr. 9, 2024, 7 pages.
First Office Action issued in corresponding Japanese Patent Application No. 2023-030811, mailed Apr. 9, 2024, 6 pages.

* cited by examiner

RESPIRATORY APPARATUS WITH MULTIPLE POWER SUPPLIES

This application is a continuation of U.S. patent application Ser. No. 16/755,096, filed on Apr. 9, 2020, which is a national phase entry under 35 U.S.C. § 371 of International Application No. PCT/AU2018/051080 filed Oct. 8, 2018 published in English, which claims priority from U.S. Provisional Patent Application No. 62/574,019, filed Oct. 18, 2017, all of which are incorporated herein by reference.

BACKGROUND OF THE TECHNOLOGY

Field of the Technology

The present technology relates to devices for the diagnosis, treatment and/or amelioration of respiratory disorders, and to procedures to prevent respiratory disorders. In particular, the present technology relates to medical devices, and their components, such as for treating respiratory disorders and for preventing respiratory disorders. Such technology may relate to components, for example, powering circuits, that enhance control or operation of such devices such as for convenience in operation or set-up with different power supplies.

Description of the Related Art

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist, such as Obstructive Sleep Apnea (OSA), Cheyne-Stokes Respiration (CSR), Obesity Hyperventilation Syndrome (OHS), Chronic Obstructive Pulmonary Disease (COPD), Neuromuscular Disease (NMD), chest wall disorders and associated respiratory failures.

Otherwise healthy individuals may take advantage of systems and devices to prevent respiratory disorders from arising.

2.2.1 Systems

One known product used for treating sleep disordered breathing is the S9 Sleep Therapy System, manufactured by ResMed. A treatment system in one form may comprise an RPT device, a humidifier, a patient interface and an air circuit.

2.2.2 Therapy

A number of therapies, such as Nasal Continuous Positive Airway Pressure (CPAP), Non-invasive ventilation (NIV), High Flow Therapy (HFT), may be used to treat one or more respiratory disorders.

2.2.3 Patient Interface

The application of a supply of air at positive pressure to the entrance of the airways of a patient is facilitated by the use of a patient interface, such as a nasal mask, full-face mask or nasal pillows. A range of patient interface devices are known, however a number of them suffer from being one or more of obtrusive, aesthetically undesirable, poorly fitting, difficult to use and uncomfortable especially when worn for long periods of time or when a patient is unfamiliar with a system. Masks designed solely for aviators, as part of personal protection equipment or for the administration of anaesthetics may be tolerable for their original application, but nevertheless be undesirably uncomfortable to be worn for extended periods, for example, while sleeping.

2.2.4 RPT Device

The air at positive pressure or high flow is typically supplied to the airway of a patient by a respiratory therapy device (RPT) such as a positive airway pressure (PAP) apparatus or device using a motor-driven blower. The outlet of the blower is connected via a flexible delivery conduit to a patient interface as described above.

Such devices can have significant power demands during therapy operations with the device. For example, powering a motor of a blower for therapy may typically require a significant amount of power (e.g., power in excess of 20, 30 or 40 watts.) In addition, such devices are sometimes provided with accessory components to form a system, for comfort conditioning of the flow or pressurized air supplied by the flow generator. For example, the supplied air may be applied to a humidifier to humidify and warm the treatment gas prior to its delivery to a patient. A humidifier typically includes a heating element. Similarly, various heating elements can be connected with a delivery conduit to help in maintaining a particular temperature of the supplied gas as it is conducted to the patient from a supply unit or humidifier. Such heating elements also require a significant amount of power such as when compared to the power requirements of a microcontroller or digital processor and memory that might be used in such device. In total, a treatment system to provide therapy may require power in excess of 90 watts, such as over 110 watts or even 120 watts.

In some situations, a therapy system may be set up by a party other than the user of the therapy system. For instance, a clinician, or a home medical equipment (HME) provider may prepare the therapy system with its initial settings for the user (e.g. the patient). In some situations, the initial set-up may be carried out multiple times in a day by one HME, such as one set-up each for a plurality of patients.

Accordingly, any improvement in ease of set-up may be not only valuable for the patient of the system, but for those performing the set-up multiple times, the benefit would be similarly amplified.

BRIEF SUMMARY OF THE TECHNOLOGY

The present technology is directed towards providing medical devices, or the components thereof, that may be used in the detection, diagnosis, amelioration, treatment, and/or prevention of respiratory conditions having one or more of improved comfort, cost, efficacy, ease of use and manufacturability.

Some embodiments of the present technology relate to apparatus used in the detection, diagnosis, amelioration, treatment or prevention of a respiratory disorder.

Some embodiments of the present technology include a respiratory apparatus or RPT device. The apparatus may include a blower configured to generate a flow of breathable gas in which the blower is on a power bus that may be coupled to a power supply that is sufficient to power the blower and a different power supply that is insufficient to power the blower. The blower may include a motor powered on a power bus or power rail of the device.

The respiratory apparatus or RPT device may be configured to be powered on in a 'low-power mode' to allow set up using a low-power power supply, without initiating therapy. The device may also be configured to be powered on in a 'high-power' mode for therapy using a high-power power supply. This can enable, for example, a user or healthcare/equipment provider to conveniently set up the device in the low-power mode such as by plugging the device to a tablet computer or a smartphone via a cable, or a low-power wireless protocol. Thus, the device may be configured to make connections with different power supplies and permit different operations depending on the type of power supply attached. This may be contrasted with a device that detects a low power condition of a single power supply (e.g., a low battery condition) and changes operation with that single power supply based on the condition (low battery) of the single power supply.

Some versions of the present technology include a respiratory therapy apparatus for controlling a therapy for a respiratory disorder. The respiratory therapy apparatus may include a power input circuit to receive one or more of a first power and a second power. The first power may be from a low-power power supply adapted to couple with the respiratory therapy apparatus. The second power may be from a high-power power supply adapted to couple with the respiratory therapy apparatus. The respiratory therapy apparatus may include a controller coupled to the power input circuit and may be configured to detect at least one of the low-power power supply and the high-power power supply. The controller may be configured to, based on detection of one of the low-power power supply and the high-power power supply, selectively activate one of a first mode of operation of the respiratory therapy apparatus and a second mode of operation of the respiratory therapy apparatus. The first mode of operation may be a non-therapy mode with the first power and the second mode of operation may be a therapy mode with the second power.

In some versions, the power input circuit may include a first supply interface and a second supply interface. The first supply interface may be configured to couple with the low-power power supply and the second supply interface may be configured to couple with the high-power power supply. In some cases, at least one of the first supply interface and the second supply interface may include a removeable coupling for a power cable. In some versions, at least one of the first supply interface and the second supply interface may include a wireless power interface. Optionally, the first supply interface and the second supply interface may each include a removeable coupling for a power cable. At least one of the first supply interface and the second supply interface may include a removeable coupling for a power and data communications cable. The power input circuit may include a first supply interface configured to couple with the low-power power supply and the high-power power supply. The first supply interface may include a removeable coupling for a power cable.

In some versions, the first mode of operation may include a communication mode for communicating data to and/or from a processor of the respiratory therapy apparatus. The communications mode comprises a setup operation for transferring one or more operation control settings into a memory of the respiratory therapy apparatus. The communications mode may include a download operation for retrieving one or more of operation control settings, diagnostic data and/or operations data from a memory of the respiratory therapy apparatus. The therapy mode may involve powering a motor of a blower for generating a flow of gas to a respiratory interface for a user. Optionally, the input power circuit may include a detection circuit. The detection circuit may include a voltage detector. The voltage detector may be configured to detect voltage indicative of power received by the power input circuit. The controller may be coupled to the detection circuit to receive a signal indicative of either one of the low-power power supply and the high-power power supply. The controller may be coupled to the detection circuit to sample a voltage signal produced by the voltage detector.

In some versions, the controller may be configured to make a comparison of a detected voltage and a predetermined threshold value and may be configured to activate one of the first mode of operation and the second mode of operation based on the comparison. The detected voltage may be indicative of power from either of the low-power power supply and the high-power power supply. Activation of the second mode of operation by the controller may include activating a switching circuit configured to route supply power to motor circuits of a blower for generating a flow of gas to a respiratory interface for a user. The switching circuit nay be coupled to the controller. The switching circuit may include a semiconductor switch.

In some versions, the input power circuit may include a voltage regulator to power the controller in the first mode of operation and the second mode of operation. The respiratory therapy apparatus may further include a blower including a motor. The motor may include a motor control circuit coupled to the controller for regulating a speed of the motor. The motor may be further coupled to a power line of the input power circuit via a switch that is activated by the controller in the second mode of operation. The controller may include a processor and memory. The processor may be programmed to control operations of the respiratory therapy apparatus in the first mode of operation and the second mode of operation.

In some versions of the respiratory therapy apparatus, the low-power power supply produces a power in a range of about 5 watts to 15 watts and the high-power power supply produces a power in a range of about 80 watts to 110 watts. The low-power power supply may include a universal serial bus (USB) power supply. The low-power power supply may include a Qi power supply.

Some versions of the present technology include a respiratory therapy system for treatment of a respiratory disorder. The respiratory therapy system may include a first set of components, comprising a memory. The respiratory therapy system may include a second set of components comprising a pressure generator configured to provide a flow of air for delivery to a patient. The respiratory therapy system may include a power interface. The respiratory therapy system may include a controller configured to determine an available power available from the power interface, and selectively allow the first set of components or both the first set and the second set of components to receive power based on a determined available power. Optionally, the controller may be configured to, if the determined available power is above a threshold, allow both the first set and the second set of components to receive power.

In some versions, the first set of components further include a display. The first set of components may further include a communications circuit. Optionally, the power interface may be configured to receive a cable. The cable may be connectable to a USB port.

Some versions of the present technology include a method for a respiratory therapy device including powering an operation mode of a respiratory therapy device using a universal serial bus cable and universal serial bus power supply. The operation mode may include accessing data of the respiratory therapy device.

Some versions of the present technology may include a respiratory therapy apparatus configured to be powered in an operation mode by a universal serial bus cable and universal serial bus power supply. The operation mode may include access to a memory of the respiratory therapy apparatus.

Some versions of the present technology include a method for a respiratory therapy device. The method may include powering an operation mode of a respiratory therapy device using a wireless power transfer apparatus. The operation mode may include accessing data of the respiratory therapy device.

Some versions of the present technology include a respiratory therapy apparatus configured to be powered in an operation mode by a wireless power transfer apparatus. The operation mode may include access to a memory of the respiratory therapy apparatus.

The subject headings used in the detailed description are included only for the ease of reference of the reader and should not be used to limit the subject matter found throughout the disclosure or the claims. The subject headings should not be used in construing the scope of the claims or the claim limitations.

Various aspects of the described example embodiments may be combined with aspects of certain other example embodiments to realize yet further embodiments. It is to be understood that one or more features of any one example may be combinable with one or more features of the other examples. In addition, any single feature or combination of features in any example or examples may constitute patentable subject matter.

Other features of the technology will be apparent from consideration of the information contained in the following detailed description.

BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:
4.1 Treatment Systems

DETAILED DESCRIPTION OF EXAMPLES OF THE TECHNOLOGY

Figure 1A:
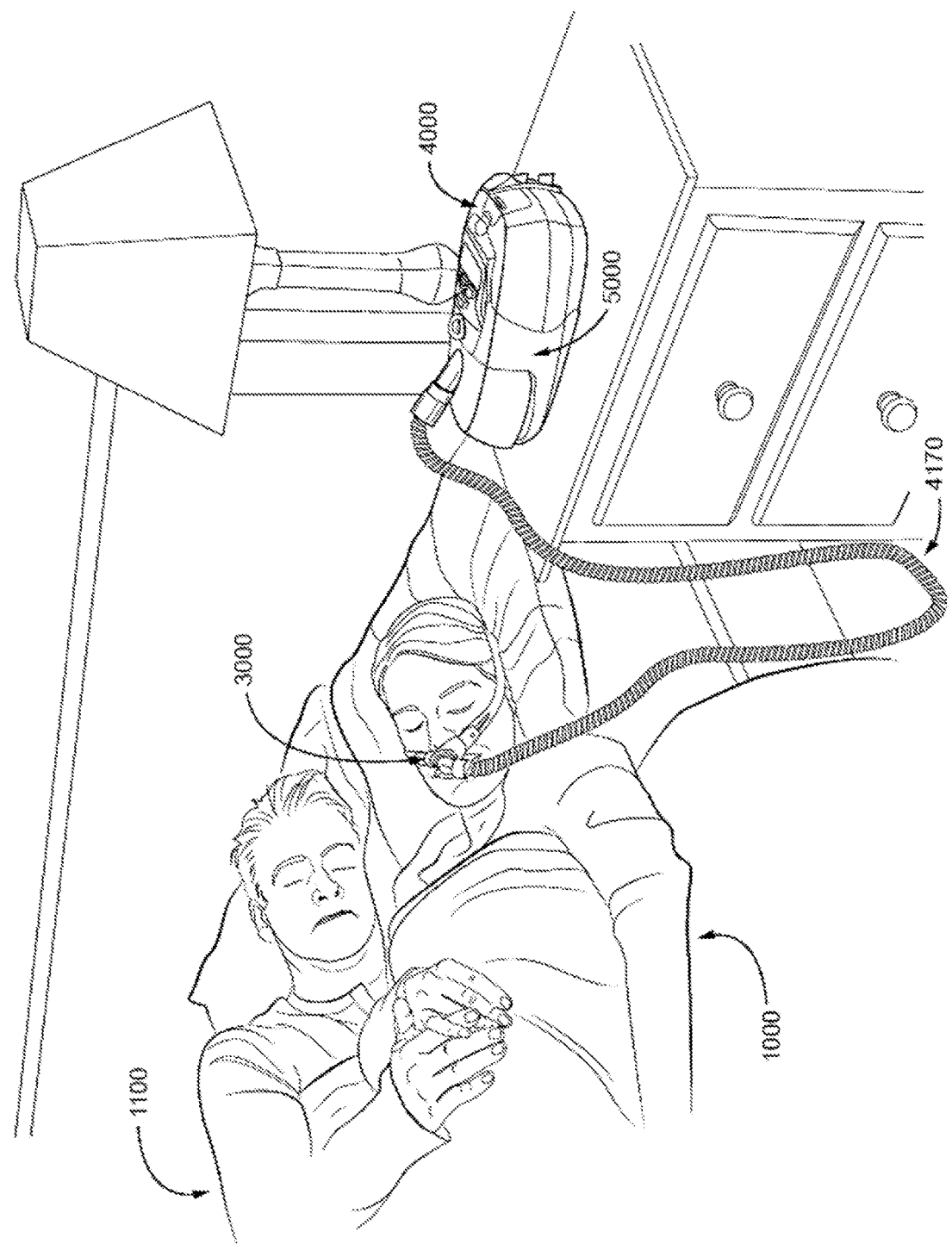
FIG. 1A shows an example therapy system. A patient 1000 wearing a patient interface 3000, receives a supply of air at positive pressure from a RPT device 4000. Air from the RPT device is humidified in a humidifier 5000, and passes along an air circuit 4170 to the patient 1000.
Figure 1B:
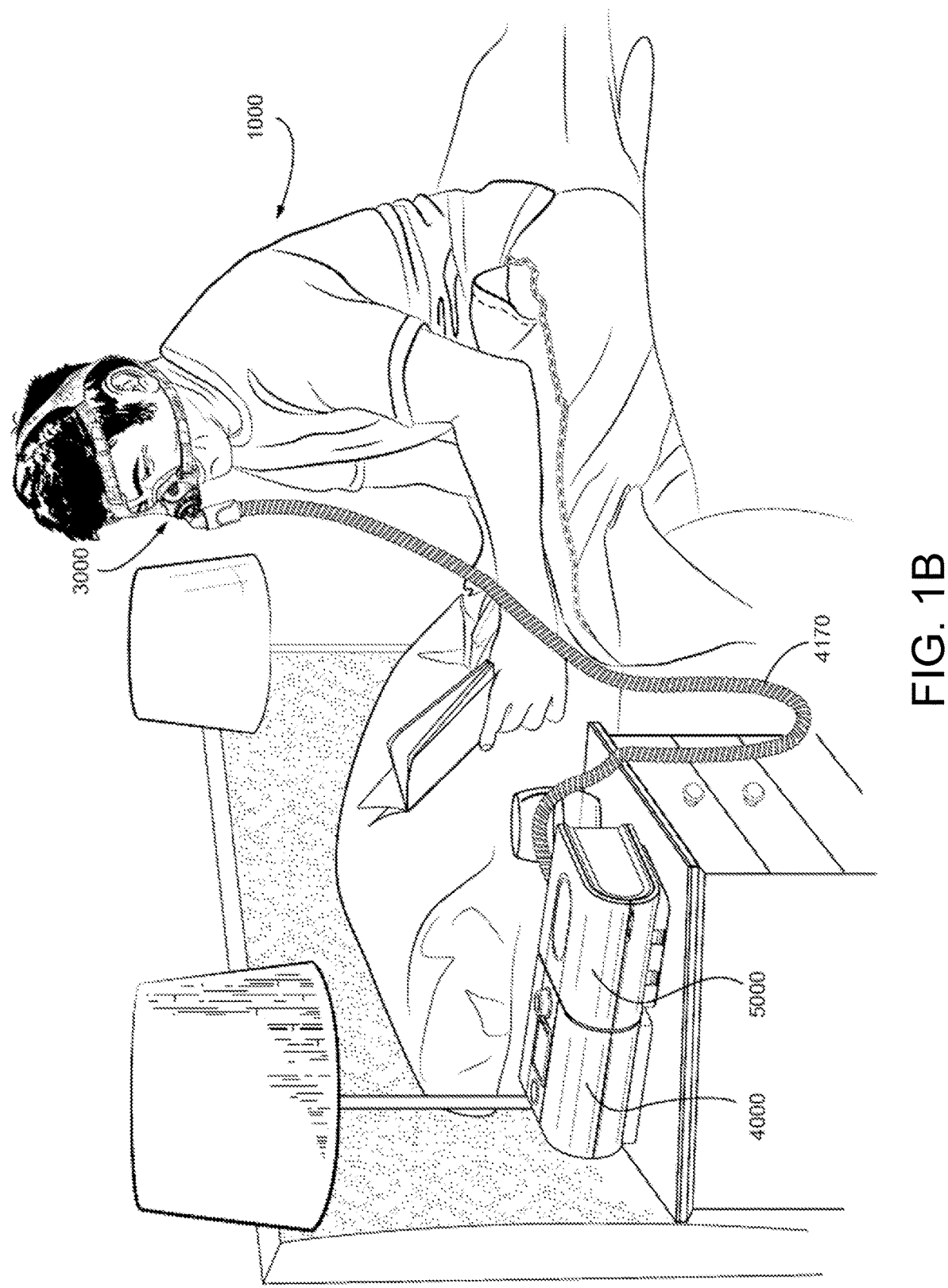
FIG. 1B shows a RPT device in use on a patient with a nasal mask.
Figure 1C:
FIG. 1C shows a RPT device in use on a patient with a full-face mask.
4.2 Therapy
4.2.1 Respiratory System
Figure 2A:
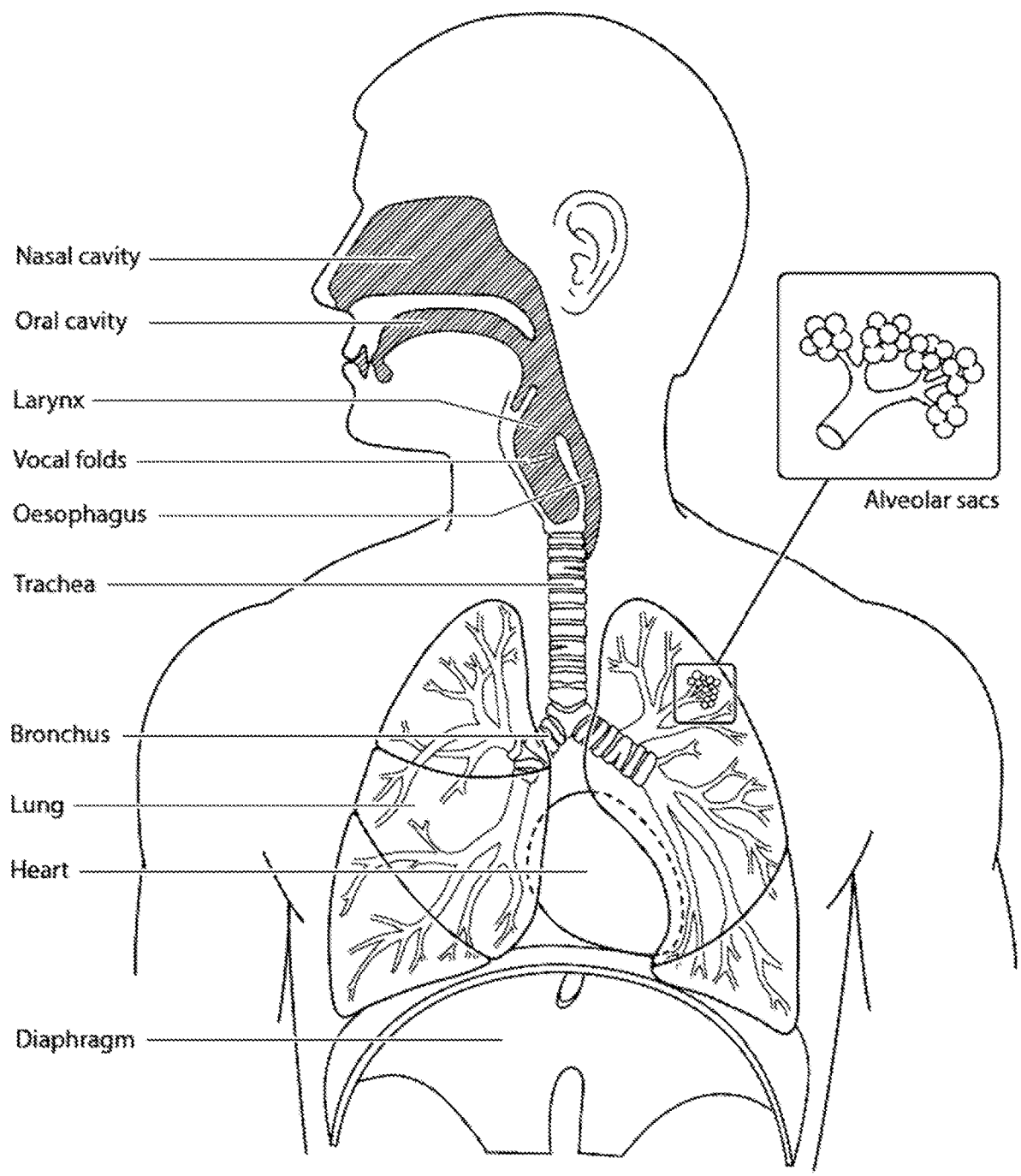
FIG. 2A shows an overview of a human respiratory system including the nasal and oral cavities, the larynx, vocal folds, oesophagus, trachea, bronchus, lung, alveolar sacs, heart and diaphragm.
4.3 Patient Interface

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

As described above, a therapy system may be set up by a third party, such as an HME provider or a clinician, who may be performing such steps multiple times in a day, multiple times during a working week. Accordingly, any improvement in efficiencies for those performing the set-up would be of great value to the provider.

By way of background, respiratory apparatus of the present technology, such as an RPT device, require power to operate. Typically, a power supply of various outputs, such as between 30 to 120 W, are used to provide the power required for RPT devices. As an example, ResMed's AirSense™ 10 device operates with a 90-Watt power supply, whether from an AC outlet, or from a battery.

Such power supplies thus typically may be bulky, and cumbersome, as it may require for example an AC to DC converter for transforming mains power to a 90 W DC power. Thus, the provider may be required to un-pack the power supply unit from the user's packaging simply to perform the set-up procedure, only to re-pack the equipment afterwards. It may be similarly undesirable to have a power supply set-up independent of the patient's device, as in such a case multiple sets of power supplies may be required for multiple manufactures, and potentially for multiple product variants for each of these manufactures.

Advantageously, respiratory apparatus of the present technology may be configured for use with different types of power supplies that may provide different power levels. The respiratory apparatus may select and provide different operation modes depending on the different power connections. Such operation mode selections may be implemented in conjunction with an input power circuit, including for example, a detection circuit as described in more detail herein. Such operation mode selections may, for example, be implemented to help users/healthcare equipment providers to quickly and conveniently set-up the respiratory device for the patient. Such an arrangement is made possible due to a realisation that to perform set-up, only a low level of power may be required, in comparison to power to provide effective respiratory therapy.

For example, an RPT device may configured to be powered on in a 'low-power mode' to allow set up where the power may be insufficient to initiate therapy because a connected power supply is not configured to provide sufficient power to power therapy operations of the RPT device. The RPT device may be configured to detect the connected power from such an external power source, and determine a mode of operation, and which of its subsystems to power on. In one example, the power source could potentially be a dedicated module, such as a ResMed 90 W power supply for the ResMed AirSense™ 10 device, that is sufficient to power all components of the RPT, or a computing device such as a tablet computer, a laptop, or a smartphone through a universal serial bus (USB) cable that is insufficient to power all components of the RPT.

For example, when a power supply designed to provide a sufficient power for all operations (e.g., a 90 W supply) is detected, the RPT device may select to operate in a 'therapy mode' and when a power supply not designed to be sufficient for all operations (e.g., a low-power 5 or 10 W availability) is detected, the RPT may operate in a 'low-power mode'.

In such a low-power mode, the RPT device may only power on a first set of subsystems, such as its controller(s) and memory, and in some cases its display and/or input/output device. The user may then be able to set or change one or more setting or operation parameters for the RPT device such as by accessing a memory of the device. Such parameter changes may be made by using the RPT display/input device itself or by making changes on a user interface of an external device (e.g., tablet computer) that in turn communicates the parameter change(s) to the RPT via a communications device of the RPT and the external device (e.g., a wired data connection or a wireless data connection).

When operating in the selected therapy mode, the RPT device may additionally power on subsystems usable or required for therapy, such as the pressure systems, humidifier and heater(s) (e.g., heated tube) etc.

When operating in the selected non-therapy (or low-power) mode, the RPT device would more simply connect to the power supply such as through a power transmission medium (e.g., a USB cable, Lightning cable, a wireless protocol (e.g. Qi), or others) to permit non-therapy operations with the RPT apparatus.

Such low power operations may be particularly advantageous for clinicians of home medical equipment (HME) providers. The operations can simplify or speed up set-up of RPT devices without requiring a particular power supply. Such operations may also allow download of data from the RPT device more easily and quickly such as for maintenance without using a particular power supply. For example, in case of hardware fault, a technician may be able to diagnose an RPT device without a risk of further damage to the device since the therapy components will not be activated with the low power supply. Upgrades to the software of the RPT may also be made, e.g., by software upload via a low power data cable, without requiring a high-power power supply.

As described in more detail herein, in some versions, a detection of the connected power supply may be implemented through detection of the voltage of a connected power source.

5.1 Treatment Systems

Accordingly, in one form, the present technology comprises apparatus for treating a respiratory disorder. The apparatus may comprise a flow generator or blower for supplying a flow of pressurised respiratory gas, such as air, to the patient 1000 via an air delivery tube leading to a patient interface 3000.

5.2 Therapy

In one form, the present technology comprises a method for treating a respiratory disorder comprising the step of applying positive pressure or high flow to the entrance of the airways of a patient 1000.

5.2.1 Nasal CPAP for OSA

In one form, the present technology comprises a method of treating Obstructive Sleep Apnea in a patient by applying nasal continuous positive airway pressure or high flow therapy to the patient.

In certain embodiments of the present technology, a supply of air at positive pressure is provided to the nasal passages of the patient via one or both nares.

5.3 Patient Interface 3000

Figure 3:
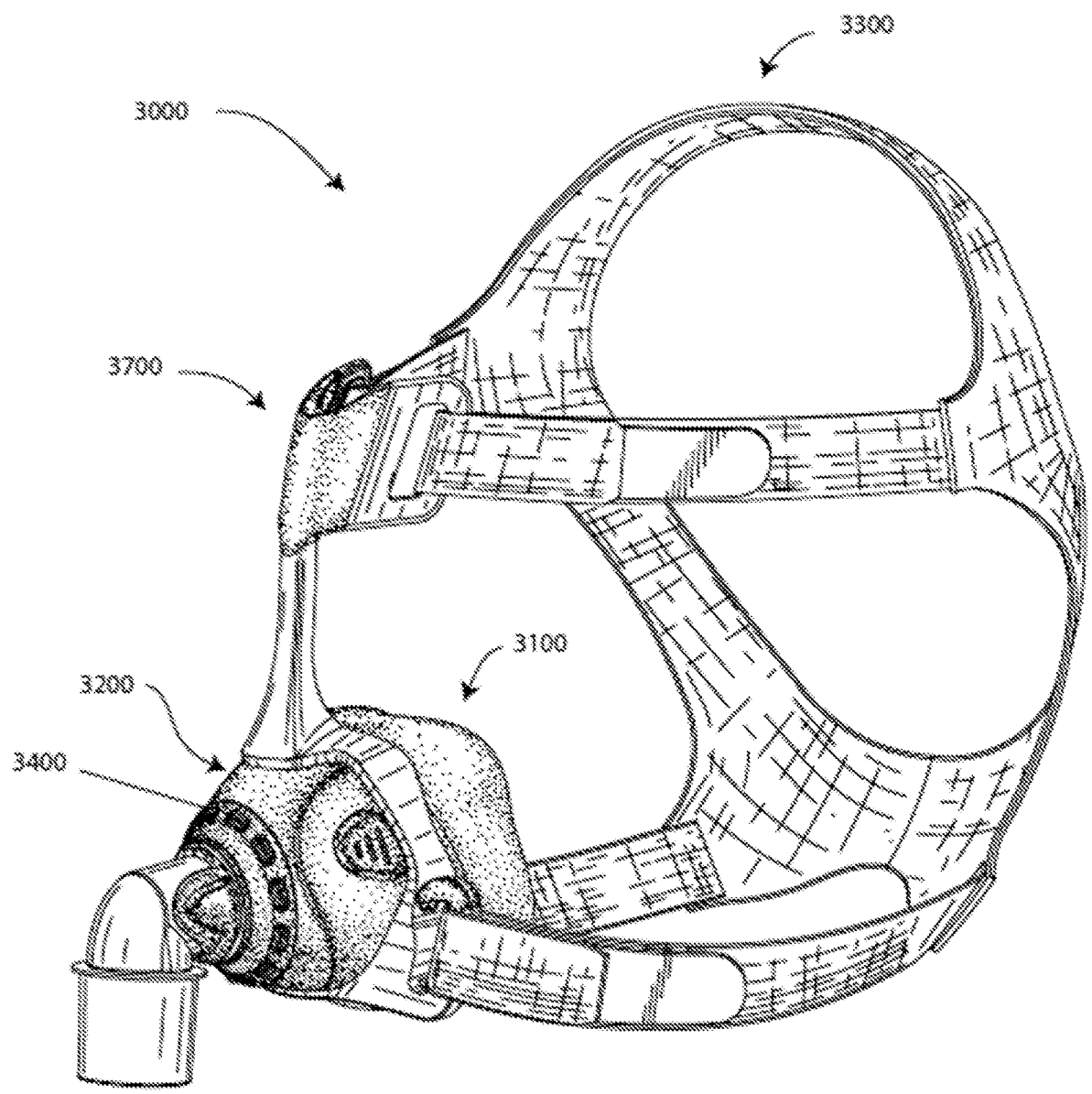
FIG. 3 shows an example patient interface.
4.4 RPT Device

With reference to FIG. 3, a non-invasive patient interface 3000 in accordance with one aspect of the present technology comprises the following functional aspects: a seal-forming structure 3100, a plenum chamber 3200, a positioning and stabilising structure 3300 and a connection port for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways. The patient interface 3000 may include a vent 3400 constructed and arranged to allow for the washout of exhaled carbon dioxide. The patient interface 3000 may include a forehead support 3700. Other types of patient interface may also be implemented such as a high flow therapy interface (e.g., nasal cannula).

5.4 RPT Device 4000

Figure 4A:
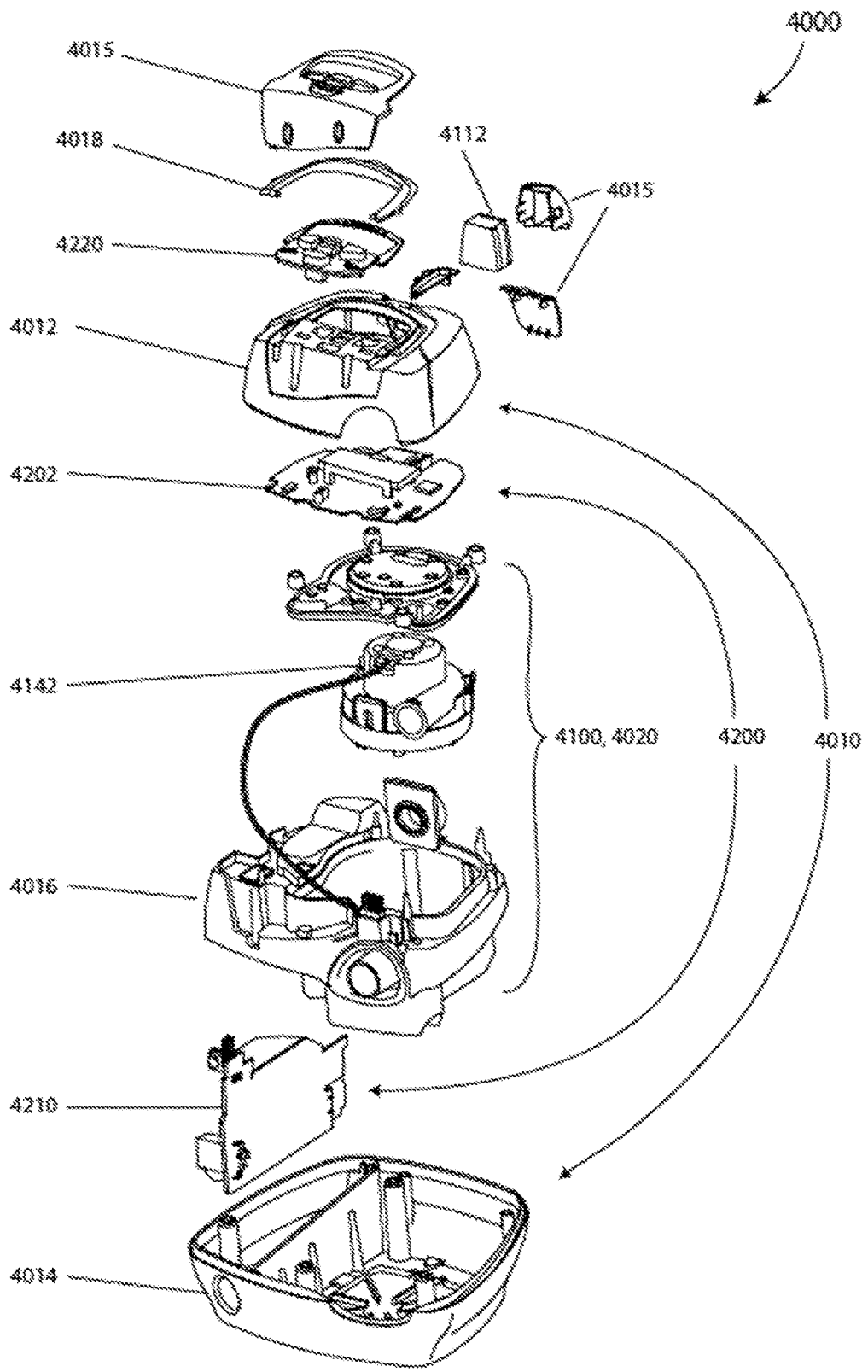
FIG. 4A shows an example RPT device.
Figure 4B:
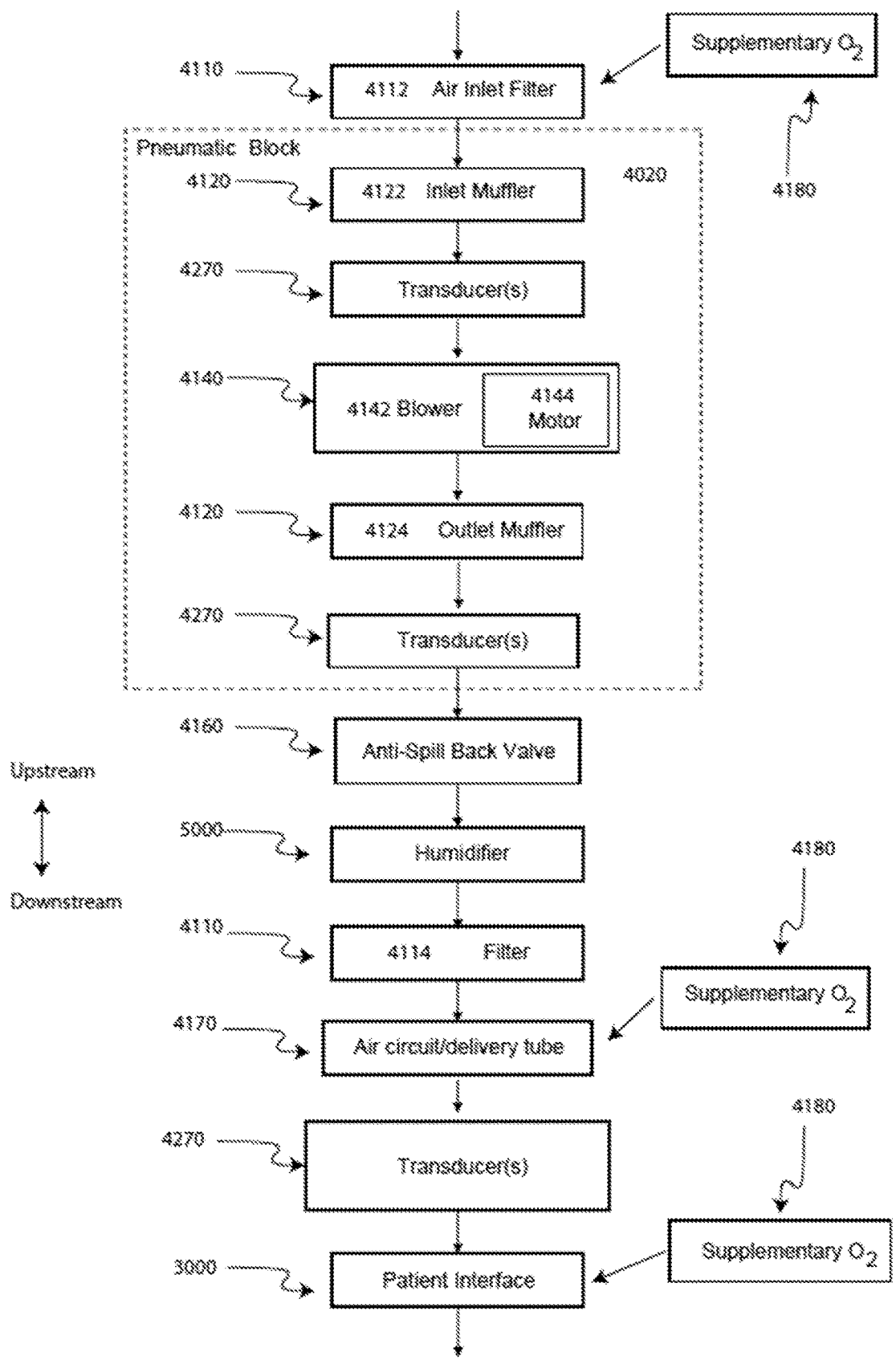
FIG. 4B shows a schematic diagram of an example pneumatic circuit of a RPT device. The directions of upstream and downstream are indicated.
Figure 4C:
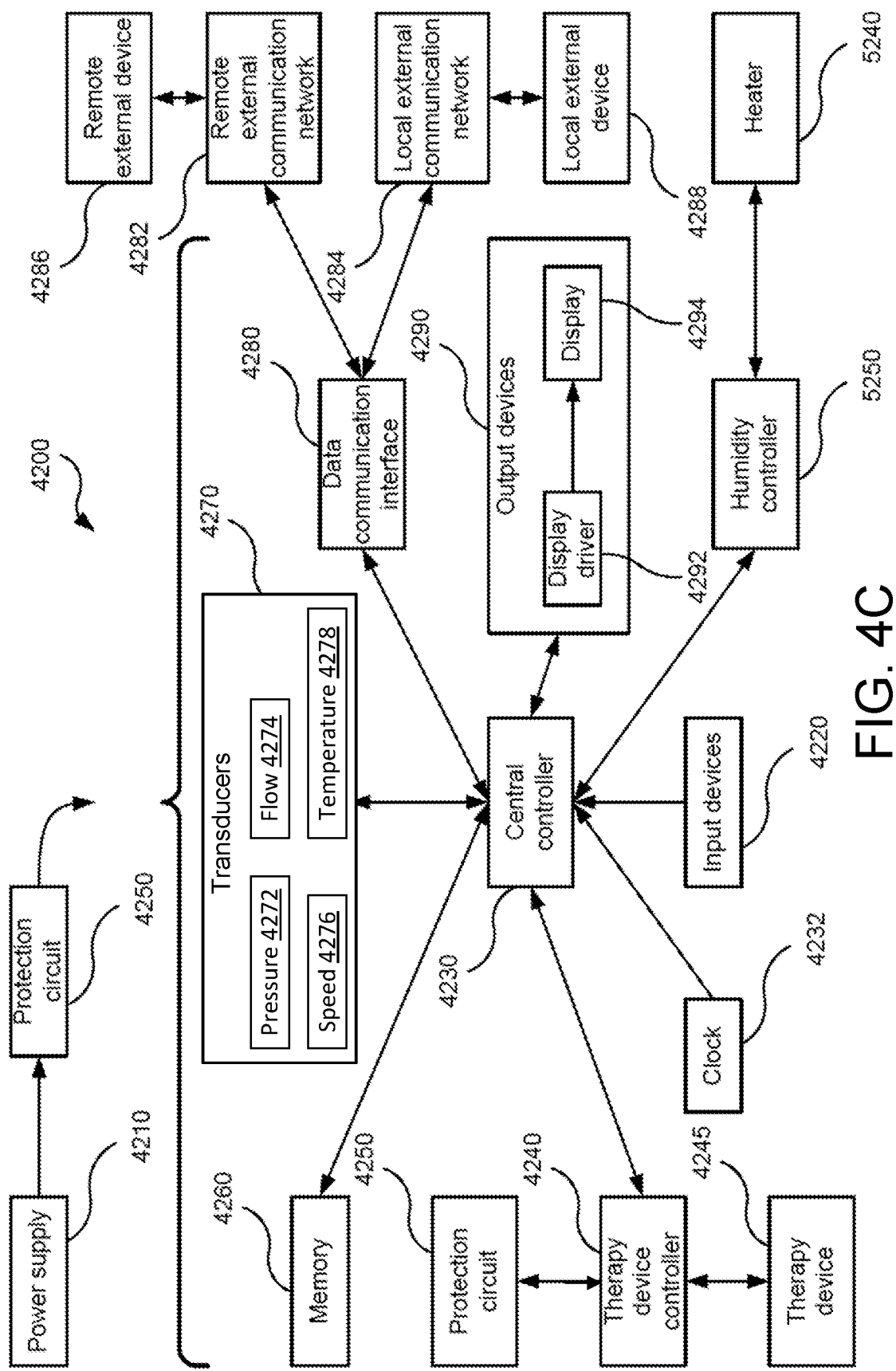
FIG. 4C shows a schematic diagram of some example electrical components of a RPT device.
Figure 4D:
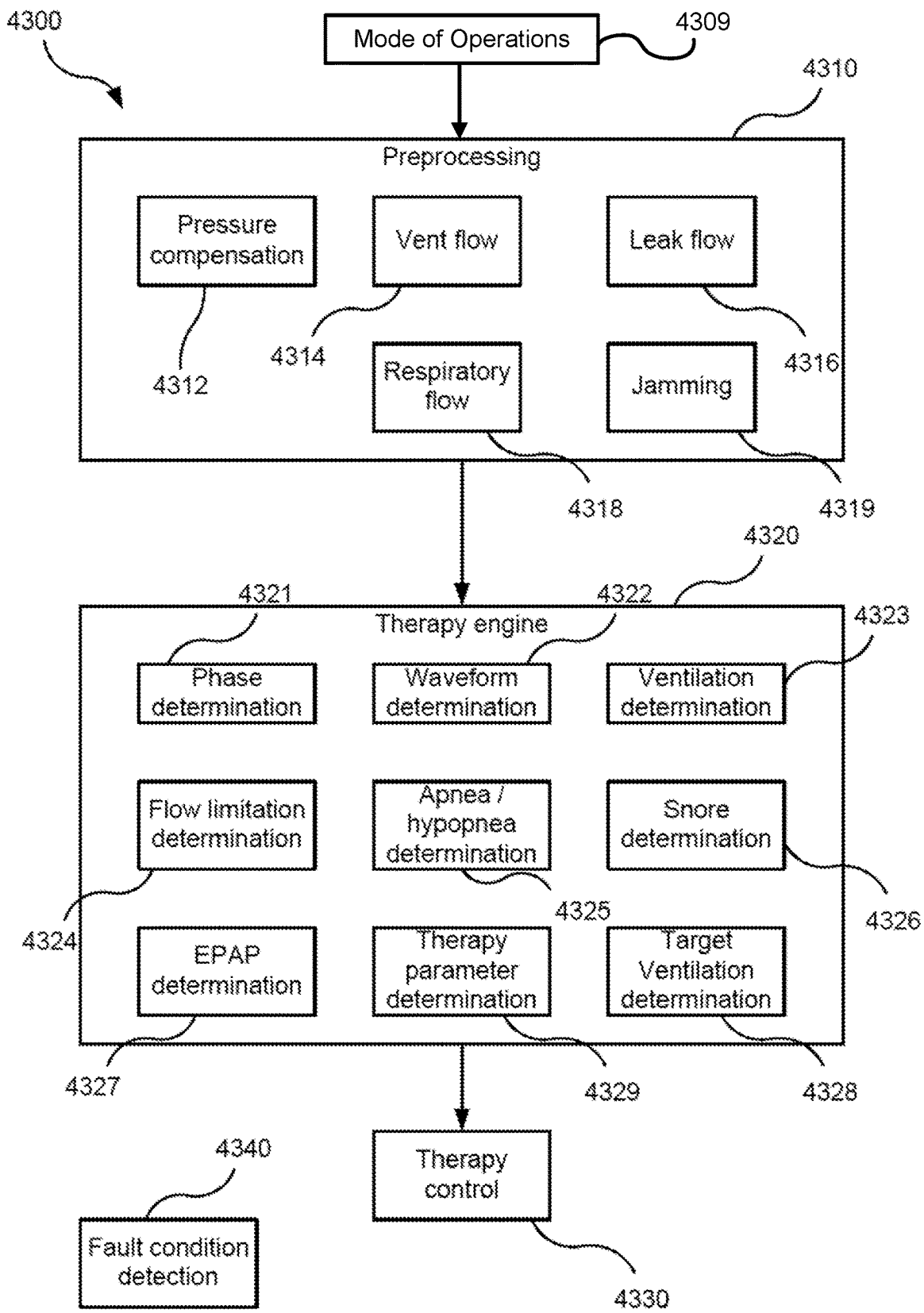
FIG. 4D shows a schematic diagram of example processes (e.g., algorithms) that may be implemented in processor or central controller of a RPT device. In this figure, arrows with solid lines indicate an actual flow of information, for example via an electronic signal.
4.5 Humidifier

With reference to FIG. 4A, a respiratory therapy apparatus such as a RPT device 4000 may include mechanical and pneumatic components 4100, electrical components 4200 and may be programmed to execute one or more algorithms 4300 (shown in FIG. 4D). As illustrated in the version of FIG. 4A, the RPT device has an external housing 4010 formed in two parts, an upper portion 4012 of the external housing 4010, and a lower portion 4014 of the external housing 4010. In alternative forms, the external housing 4010 may include one or more panel(s) 4015. The RPT device 4000 comprises a chassis 4016 that supports one or more internal components of the RPT device 4000. In one form a pneumatic block 4020 is supported by, or formed as part of the chassis 4016. The RPT device 4000 may include a handle 4018.

Referring to FIG. 4B, the pneumatic path of the RPT device 4000 comprises an inlet air filter 4112, an inlet muffler 4122, a controllable flow or pressure device 4140 capable of supplying air at positive pressure (preferably a blower 4142), and an outlet muffler 4124. One or more pressure sensors and flow sensors are included in the pneumatic path.

The pneumatic block 4020 may include a portion of the pneumatic path that is located within the external housing 4010.

With reference to FIG. 4C, electronic components 4200 of the RPT device 4000 may include an electrical power supply 4210, one or more input devices 4220, a central controller 4230, a therapy device controller 4240, a therapy device 4245, one or more protection circuits 4250, memory 4260, transducers 4270, data communication interface 4280 and one or more output devices 4290. Electrical components 4200 may be mounted on a single Printed Circuit Board Assembly (PCBA) 4202 as illustrated in FIG. 4A. In an alternative form, the RPT device 4000 may include more than one PCBA 4202.

Referring to FIG. 4D, the central controller 4230 of the RPT device 4000 is programmed to execute one or more algorithm 4300 modules, including in one implementation a mode of operations detection module 4309, a pre-processing module 4310, a therapy engine module 4320, a pressure control module 4330, and a fault condition detection module 4340.

According to some aspects of the present technology, the central controller 4230 may optionally omit the fault condition action module 4340. Moreover, fault detection may be performed by a fault mitigation integrated circuit separate from, and optionally in addition to, the central controller 4230.

In one form, the RPT device 4000 may be referred to interchangeably as a ventilator.

5.4.1 RPT Device Mechanical & Pneumatic Components 4100

5.4.1.1 Air Filter(s) 4110

With reference to FIG. 4B, a RPT device in accordance with one form of the present technology may include an air filter 4110, or a plurality of air filters 4110 (e.g., filters 4112 and 4114).

5.4.1.2 Muffler(s) 4120

In one form of the present technology, an inlet muffler 4122 is located in the pneumatic path upstream of a blower 4142. See FIG. 4B.

In one form of the present technology, an outlet muffler 4124 is located in the pneumatic path between the blower 4142 and a patient interface 3000. See FIG. 4B.

5.4.1.3 Pressure Device 4140

With reference to FIG. 4B, in one form of the present technology, a flow or pressure device 4140 for producing a flow of air at positive pressure is a controllable blower 4142. For example, the blower may include a brushless DC electric motor 4144 with one or more impellers housed in a volute. The blower is capable of delivering a supply of air, for example about 120 litres/minute, at a positive pressure in a range from about 4 $cmH_2O$ to about 20 $cmH_2O$, or in other forms up to about 30 $cmH_2O$.

The flow or pressure device 4140 is under the control of the therapy device controller 4240.

5.4.1.4 Transducer(s) 4270

With continued reference to FIG. 4B, in one form of the present technology, one or more transducers 4270 are located upstream of the pressure device 4140. The one or more transducers 4270 are constructed and arranged to measure properties of the air at that point in the pneumatic path.

In one form of the present technology, one or more transducers 4270 are located downstream of the pressure device 4140, and upstream of the air circuit 4170. The one or more transducers 4270 are constructed and arranged to measure properties of the air at that point in the pneumatic path.

In one form of the present technology, one or more transducers 4270 are located proximate to the patient interface 3000.

5.4.1.5 Anti-Spill Back Valve 4160

An anti-spill back valve may be constructed and arranged to reduce the risk that water will flow upstream from the humidifier 5000.

5.4.1.6 Air Circuit 4170

As shown in FIG. 4B, an air circuit 4170 in accordance with an aspect of the present technology is constructed and arranged to allow a flow of air or breathable gasses between the pneumatic block 4020 and the patient interface 3000.

5.4.1.7 Oxygen Delivery

With continued reference to FIG. 4B, in one form of the present technology, supplemental oxygen 4180 is delivered to a point in the pneumatic path.

5.4.2 RPT Device Electrical Components 4200

5.4.2.1 RPT Device 5.4.2.1.1 One or More Power Supply 4210

Referring to FIG. 4C and FIGS. 6 through 10, power supply 4210 (PS1) supplies power to the other components of the typical RPT device 4000, such as, the input device 4220, the central controller 4230, the therapy device 4245, and the output device 4290, heater(s) etc.

In one form of the present technology power supply 4210 provides electrical power to the RPT device 4000 without a humidifier. In another form of the present technology, power supply 4210 provides electrical power to both RPT device 4000 and humidifier 5000. In a yet another form, power supply 4210 provides electrical power to RPT device 4000, humidifier 5000 and an air circuit 4170, wherein the air circuit 4170 comprises a heating element.

In one form of the present technology, power supply 4210 is internal to the external housing 4010 of the RPT device 4000. In another form of the present technology, power supply 4210 is external of the external housing 4010 of the RPT device 4000 (sometimes referred herein as the RPT).

However, as illustrated in FIG. 6-9, the RPT may be configured to operate with different power supplies. For example, it may be configured to operate with two different power supplies, such as two power supplies with varying or different power output levels. Moreover, it may be configured to provide different operations depending on which of the different power supplies is connected to the RPT. In some versions, as discussed in more detail herein, a mode of operation of the device may be determined by a controller or processor of the RPT depending on the type (or power level) of the power supply attached to the RPT.

For example, the power supply 4210 (PS1) may include a Mains powered switched-mode power supply, which may block negative regenerative currents. In some versions, the power supply 4210 may be a high-power power supply, such as an internal or external power supply, configured to provide power in a range of approximately 60 to 120 watts, such as a 90-watt power supply. The external power supply may be plugged into an interface 6711 (e.g., a power interface 6711A having wire(s) for only power or a combined data/power interface 6711B having wires for data and power) of the RPT such as with a cable connecting the power supply to the RPT. The external power supply (or the internal power supply) may then also be plugged into a Mains power outlet. In the case of the internal power supply, a cable may be plugged into a Mains outlet so as to connect an AC input of the internal power supply to the Mains outlet, which is more directly integrated with the power bus of the RPT. The internal or external power supply may be a AC to DC converter which converts the AC Mains input to a DC output for powering the RPT.

Such an external or internal power supply may be configured to convert the input of the power supply to an output DC signal such as 12 or 24 volts, but may be preferably 24 volts approximately. In some versions, the external power supply may be a DC/DC convertor such as a convertor that may accept an input of 12 volt and/or 24 volts DC and convert that to a DC power signal of 12 volts or 24 volts for the RPT. In a typical example, the output DC power signal from the external power supply may be a 24-volt signal.

Such a power supply may be considered a power supply that produces a high power in that it is especially able to provide sufficient power to operate the RPT in its therapy mode(s) such as when the device is providing a flow of pressurized breathable gas by powering a motor of a blower (e.g., a therapy device controller 4240 and therapy device 4245 including any necessary sensor(s)) which may optionally include humidification (e.g., humidity controller 5250 and heater 5240) and/or other heater devices (e.g., tube heater). Typically, such a high-power power supply is sufficient to power all operations of the RPT, as a system.

However, in some versions as discussed in more detail herein, other power supplies may optionally be utilized with the RPT of the present technology. For example, the RPT may be configured to couple via an interface with an alternate power supply 4210-ALT (PS2). Such an alternate power supply may be considered a low-power or reduced-power power supply because it produces insufficient power to power all operations of the RPT and is especially insufficient to power the therapy operations of the RPT. Such an external low-power power supply may be configured to provide power in a range of, for example, about 5 watts to 15 watts, such as 10 watts. In a typical example, the output DC power signal from such a low-power external power supply may be a 5-volt signal. Typically, such a low-power external power supply is sufficient to power a controller and a memory (e.g., central controller 4230) and may also power a communications circuit (e.g., data communication interface 4280) of the RPT. In some cases, it may also be sufficient to power one or more output device 4290 (e.g., a display) and one or more input device 4220 (e.g., a keypad) of the RPT. The low-power external power supply may be plugged into an interface 6711 (e.g., a power interface 6711A having wire(s) for only power or a combined data/power interface 6711B having wires for data and power) of the RPT such as with a cable connecting the power supply to the RPT. The combined data/power interface 6711B may for example be a Universal Serial Bus (USB) connector port such as a type A, type B or type C connector port, micro-USB connector port, lightning connector port, or other suitable connector port. Thus, in some cases, such a cable connection may serve not only as a power transfer conduit for the RPT but may also serve as a data transfer conduit/bus. Example low-power external power supply may include, for example, a Universal Serial Bus (USB) hub, a USB port power supply adapter, a USB port of a processing device, such as a desktop computer, laptop computer, tablet computer, etc. Thus, a USB cable or a Lightning cable may be used to connect the RPT device and the alternate power supply 4210-ALT.

In some versions, the RPT may be configured to couple via an interface 6711 (e.g., wireless power interface 6711C shown in FIG. 8) with an alternate power supply 4210-ALT to receive a wireless power. In such a case, the alternate power supply 4210-ALT may be a wireless power supply. For example, such an interface may receive power by electromagnetic induction, resonant inductive coupling, magnetic resonance or inductive power transfer (IPT). In such cases, the interface may include a receiver coil and a receiver circuit to receive a magnetic field from a transmitter coil of the alternate power supply 4210-ALT and thereby produce DC power in the RPT. The transmitter coil may be operated by the alternate power supply so that when it is proximate the interface 4211, the alternate power supply may serve as a low or reduced-power power supply for the RPT device 4000 as previously discussed. In some such versions, the alternate power supply 4210-ALT may be a power supply configured in accordance with the Qi standard. In some versions, the coils may be planar. Thus, the RPT may have a set of planar receiver coils such as on a bottom housing of the RPT so that it may be set down over a wireless alternate power supply with planar coils for the power transfer. As previously described, such a wireless external power supply may, for example, be sufficient to power a controller, including a memory, (e.g., central controller 4230) and may also power a communications circuit (e.g., data communication interface 4280) of the RPT. However, it may also optionally be configured to power a display and input device of the RPT.

Figure 7:
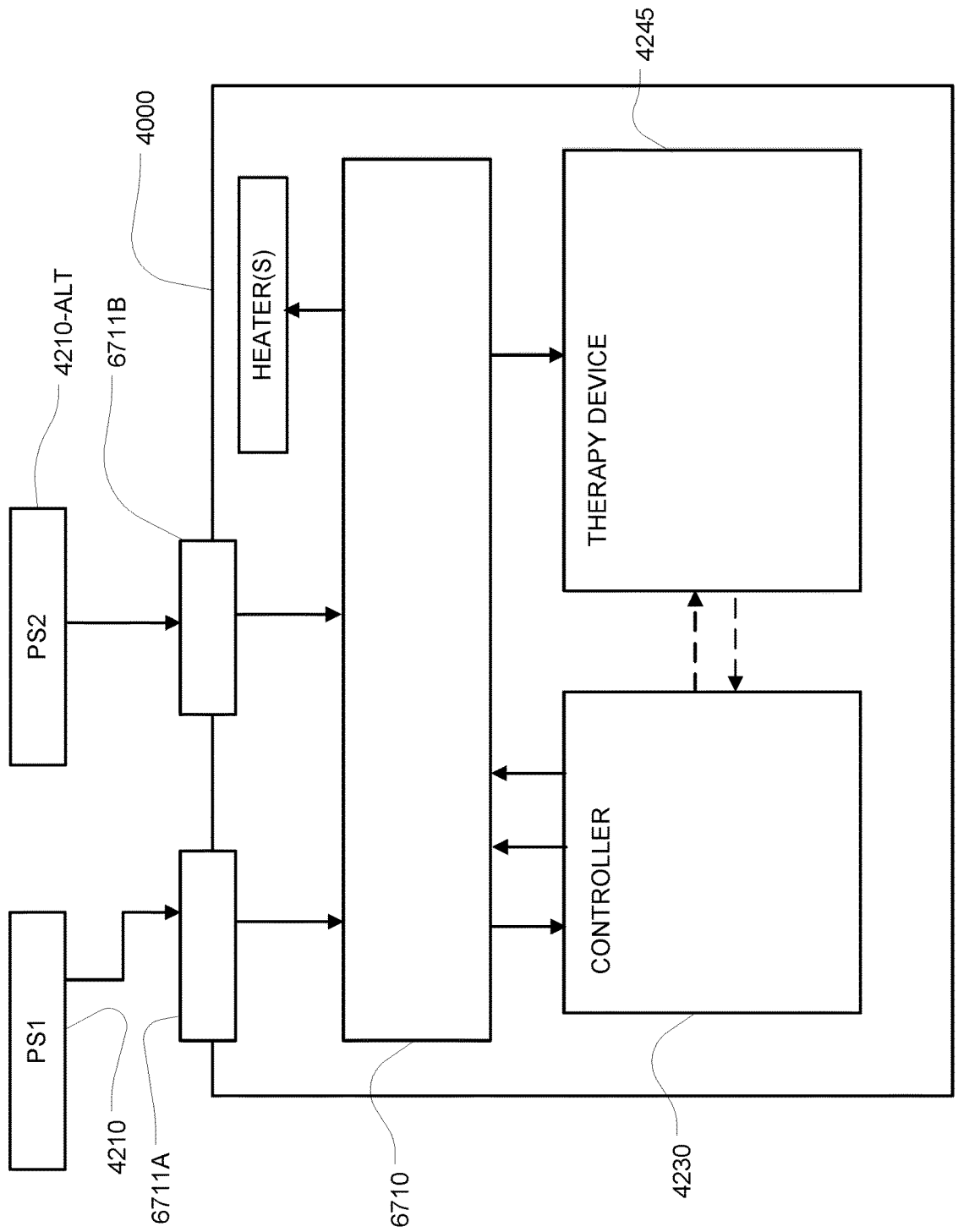
FIG. 7 is another schematic diagram of aspects of a RPT device showing a configuration with an input power circuit for different power supply operations using multiple power input interfaces in accordance with one aspect of the present technology.
Figure 8:
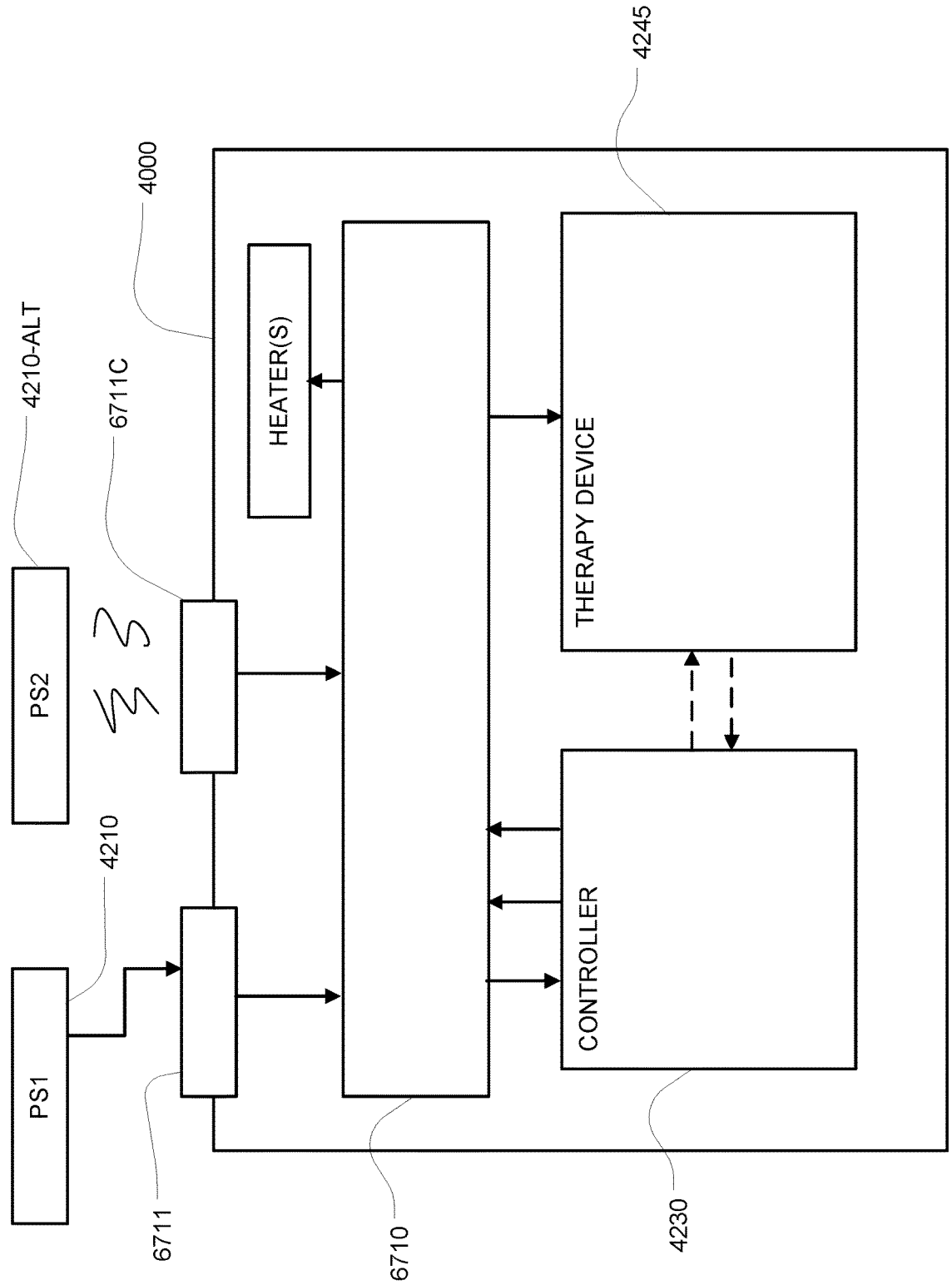
FIG. 8. is another schematic diagram of aspects of a RPT device showing a configuration with an input power circuit for different power supply operations including a wireless power input interface in accordance with one aspect of the present technology.

In some forms, the RPT device may be configured to couple with a plurality of power supplies 4210 simultaneously, such as shown in FIG. 7, to 4210 (PS1) and 4210-ALT (PS2). In such an arrangement, the RPT device may be configured to prioritise one power supply over another, such as preferring a power supply capable of higher power.

Additionally, the RPT device may be configured to communicate with an external device connected through a second power supply, while receiving power from a first power supply. For example, the RPT device may be simultaneously coupled with a high-powered (e.g. Mains powered switched-mode) power supply and a low-powered (e.g. from a tablet computer) power supply, in which configuration the RPT device may be configured to receive power from the high-powered power supply, and communicate with the tablet computer. For instance, the user may perform set-up procedures using the tablet computer while the RPT device is powered from the high-powered power supply. The RPT device may be further configured, for example, that upon disconnection of the high-powered power supply, it would begin to receive power from the low-powered power supply.

5.4.2.1.2 Input Device(s) 4220

Input devices 4220 (shown in FIG. 4C) may include one or more of buttons, switches or dials to allow a person to interact with the RPT device 4000. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

5.4.2.1.3 Central Controller 4230

In one form of the present technology, a central controller 4230 (shown in FIG. 4C) is a dedicated electronic circuit configured to receive input signal(s) from the input device 4220, and to provide output signal(s) to the output device 4290 and/or the therapy device controller 4240 and/or a humidifier controller.

In one form, the central controller 4230 is an application-specific integrated circuit. In another form, the central controller 4230 may be formed with discrete electronic components.

In one form of the present technology, the central controller 4230 (shown in FIG. 4C) may be a processor 4230P or a microprocessor, suitable to control a RPT device 4000 such as an x86 INTEL processor.

The central controller 4230 suitable to control a RPT device 4000 in accordance with another form of the present technology includes a processor based on ARM Cortex-M processor from ARM Holdings. For example, an STM32 series microcontroller from ST MICROELECTRONICS may be used.

In a further alternative form of the present technology, the central controller 4230 may include a member selected from the family ARM9-based 32-bit RISC CPUs. For example, an STR9 series microcontroller from ST MICROELECTRONICS may be used.

In certain alternative forms of the present technology, a 16-bit RISC CPU may be used as the central controller 4230 for the RPT device 4000. For example, a processor from the MSP430 family of microcontrollers, manufactured by TEXAS INSTRUMENTS, may be used.

The central controller 4230 is configured to receive input signal(s) from one or more transducers 4270, and one or more input devices 4220. The central controller 4230 may also be configured with one or more digital or analog input ports as previously described such as for implementing the mode of operations detection module 4309 in conjunction with the operations of the input power circuit 6710.

The central controller 4230 is configured to provide output signal(s) to one or more of an output device 4290, a therapy device controller 4240, a data communication interface 4280 and humidifier controller 5250. Thus, the central controller 4230 may also be configured with one or more digital or analog output ports as previously described such as for implementing the mode of operations detection module 4309 in conjunction with the switching operations of the input power circuit 6710.

The central controller 4230, or multiple such processors, is configured to implement the one or more methodologies described herein such as the one or more algorithms 4300 (shown in FIG. 4D) expressed as computer programs stored in a computer readable storage medium, such as memory 4260. In some cases, as previously discussed, such processor(s) may be integrated with a RPT device 4000. However, in some devices the processor(s) may be implemented discretely from the flow generation components of the RPT device, such as for purpose of performing any of the methodologies described herein without directly controlling delivery of a respiratory therapy. For example, such a processor may perform any of the methodologies described herein for purposes of determining control settings for a ventilator or other respiratory related events by analysis of stored data such as from any of the sensors described herein. Such a processor may also perform any of the methodologies relating to the different mode of operations concerning the different types of power supplies as described in more detail herein.

5.4.2.1.4 Therapy Device 4245

In one form of the present technology, the therapy device 4245 (shown in FIG. 4C) is configured to deliver therapy to a patient 1000 under the control of the central controller 4230. The therapy device 4245 may be the controllable flow or pressure device 4140, such as a positive air pressure device 4140. Such a device may be implemented with a blower, such as a servo-controlled blower. Such a blower may be implemented with a motor having an impeller in a volute.

5.4.2.1.5 Therapy Device Controller 4240

In one form of the present technology, therapy device controller 4240 (shown in FIG. 4C) is a therapy control module 4330 (shown in FIG. 4D) that may implement features of the algorithms 4300 executed by or in conjunction with the central controller 4230. In some cases, the therapy device controller 4240 may be implemented with a motor drive.

In one form of the present technology, therapy device controller 4240 is a dedicated motor control integrated circuit. For example, in one form a MC33035 brushless DC motor controller, manufactured by ONSEMI is used.

5.4.2.1.6 Protection Circuits 4250

Preferably a RPT device 4000 in accordance with the present technology includes one or more protection circuits 4250 such as shown in FIG. 4C.

One form of protection circuit 4250 in accordance with the present technology is an electrical protection circuit.

One form of protection circuit 4250 in accordance with the present technology is a temperature or pressure safety circuit.

In some versions of the present technology, a protection circuit 4250 may include a transient absorption diode circuit 4400. The circuit may be configured to absorb energy generated or converted from rotational kinetic energy, such as from the blower motor. According to another aspect of the present technology, a protection circuit 4250 may include a fault mitigation integrated circuit.

5.4.2.1.7 Memory 4260

In accordance with one form of the present technology the RPT device 4000 includes memory 4260 (shown in FIG. 4C), preferably non-volatile memory. In some forms, memory 4260 may include battery powered static RAM. In some forms, memory 4260 may include volatile RAM.

Preferably memory 4260 is located on PCBA 4202 (shown in FIG. 4A). Memory 4260 may be in the form of EEPROM, or NAND flash.

Additionally or alternatively, RPT device 4000 includes removable form of memory 4260, for example a memory card made in accordance with the Secure Digital (SD) standard.

In one form of the present technology, the memory 4260 acts as a computer readable storage medium on which is stored computer program instructions expressing the one or more methodologies described herein, such as the one or more algorithms 4300.

5.4.2.1.8 Transducers 4270

Transducers 4270 (shown in FIG. 4C) may be internal to the device, or external to the RPT device. External transducers may be located for example on or form part of the air delivery circuit, and/or the patient interface. External transducers may be in the form of non-contact sensors such as a Doppler radar movement sensor that transmit or transfer data to the RPT device.

5.4.2.1.8.1 Flow

A flow transducer 4274 (shown in FIG. 4C) in accordance with the present technology may be based on a differential pressure transducer, for example, an SDP600 Series differential pressure transducer from SENSIRION. The differential pressure transducer is in fluid communication with the pneumatic circuit, with one of each of the pressure transducers connected to respective first and second points in a flow restricting element.

In use, a signal representing total flow Qt from the flow transducer 4274 is received by the central controller 4230. However, other sensors for producing such a flow signal or estimating flow may be implemented. For example, a mass flow sensor, such as a hot wire mass flow sensor, may be implemented to generate a flow signal in some embodiments. Optionally, flow may be estimated from one or more signals of other sensors described here, such as in accordance with any of the methodologies described in a U.S. patent application Ser. No. 12/192,247, the disclosure of which is incorporated herein by reference.

5.4.2.1.8.2 Pressure

A pressure transducer 4272 (shown in FIG. 4C) in accordance with the present technology is located in fluid communication with the pneumatic circuit. An example of a suitable pressure transducer is a sensor from the HONEYWELL ASDX series. An alternative suitable pressure transducer is a sensor from the NPA Series from GENERAL ELECTRIC.

In use, a signal from the pressure transducer 4272 is received by the central controller 4230. In one form, the signal from the pressure transducer 4272 is filtered prior to being received by the central controller 4230.

5.4.2.1.8.3 Motor Speed

In one form of the present technology a motor speed signal from a motor speed transducer 4276 (shown in FIG. 4C) is generated. A motor speed signal is preferably provided by therapy device controller 4240. Motor speed may, for example, be generated by a speed sensor, such as a Hall Effect sensor.

5.4.2.1.8.4 Temperature

The temperature transducer 4278 (shown in FIG. 4C) may measure temperature of the gas in the pneumatic circuit. One example of the temperature transducer 4278 is a thermocouple or a resistance temperature detector (RTD).

5.4.2.1.9 Data Communication Systems

In one preferred form of the present technology, a data communication interface 4280 (shown in FIG. 4C) is provided, and is connected to the central controller 4230. Data communication interface 4280 is preferably connectable to remote external communication network 4282. Data communication interface 4280 is preferably connectable to local external communication network 4284. Preferably remote external communication network 4282 is connectable to remote external device 4286. Preferably local external communication network 4284 is connectable to local external device 4288. The data communications interface may optionally include the data/power interface 6711B and/or a wireless communications interface (e.g., a transceiver using a wireless protocol such as Bluetooth, WIFI, Bluetooth LE etc.).

In one form, data communication interface 4280 is part of the central controller 4230. In another form, data communication interface 4280 is an integrated circuit that is separate from the central controller 4230.

In one form, remote external communication network 4282 is the Internet. The data communication interface 4280 may use wired communication (e.g. via Ethernet, or optical fibre) or a wireless protocol to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

Preferably local external device 4288 is a personal computer, mobile phone, tablet or remote control.

5.4.2.1.10 Output Devices Including Optional Display, Alarms

An output device 4290 (shown in FIG. 4C) in accordance with the present technology may take the form of one or more of a visual, audio and haptic unit. A visual display may be a Liquid Crystal Display (LCD) or Light Emitting Diode (LED) display.

5.4.2.1.10.1 Display Driver 4292

A display driver 4292 (shown in FIG. 4C) receives as an input the characters, symbols, or images intended for display on the display 4294, and converts them to commands that cause the display 4294 to display those characters, symbols, or images.

5.4.2.1.10.2 Display 4294

A display 4294 (shown in FIG. 4C) is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.4.3 Input Power Circuit 6710

In order to accommodate a reception of power from the different power supplies as previously described, the RPT may include an input power circuit 6710. The input power circuit 6710 will typically be connected to the interface 6711 (e.g., power interface 6711A, data/power interface 6711B and/or wireless power interface 6711C) for the power supplies (PS1 and/or PS2). The input power circuit 6710 can include circuit components for receiving and routing the power of the one or more power supplies to some or all of the components of the RPT depending on the power supply. For example, the circuit 6710 may permit routing of power, such as via power rails, from the power supply 4210 to permit powering of all of the components (e.g., therapy generating components) of the RPT such as when the high-power power supply (PS1) is connected to the RPT.

The circuit 6710 may also permit routing of power from the alternate power supply 4210-ALT (PS2), such as via power rails, to a subset of the components of the RPT for only powering a subset of the components of the RPT. Such a subset may be low power components of the RPT. For example, the subset of the components may include a controller such as the central controller 4230 or other processor components of the RPT. Such a subset may include a communications circuit (e.g., communications interface 4280) such as for wired or wireless communication of data to and from the RPT. Such a subset will typically exclude the higher power consuming components of the RPT such as the therapy device (e.g., motor inverter bridge, motor and/or therapy device controller) and heating components (e.g., humidifier heater, tube heater etc.) that are used during therapy or other operation that uses the therapy devices and/or heating components.

Figure 9:
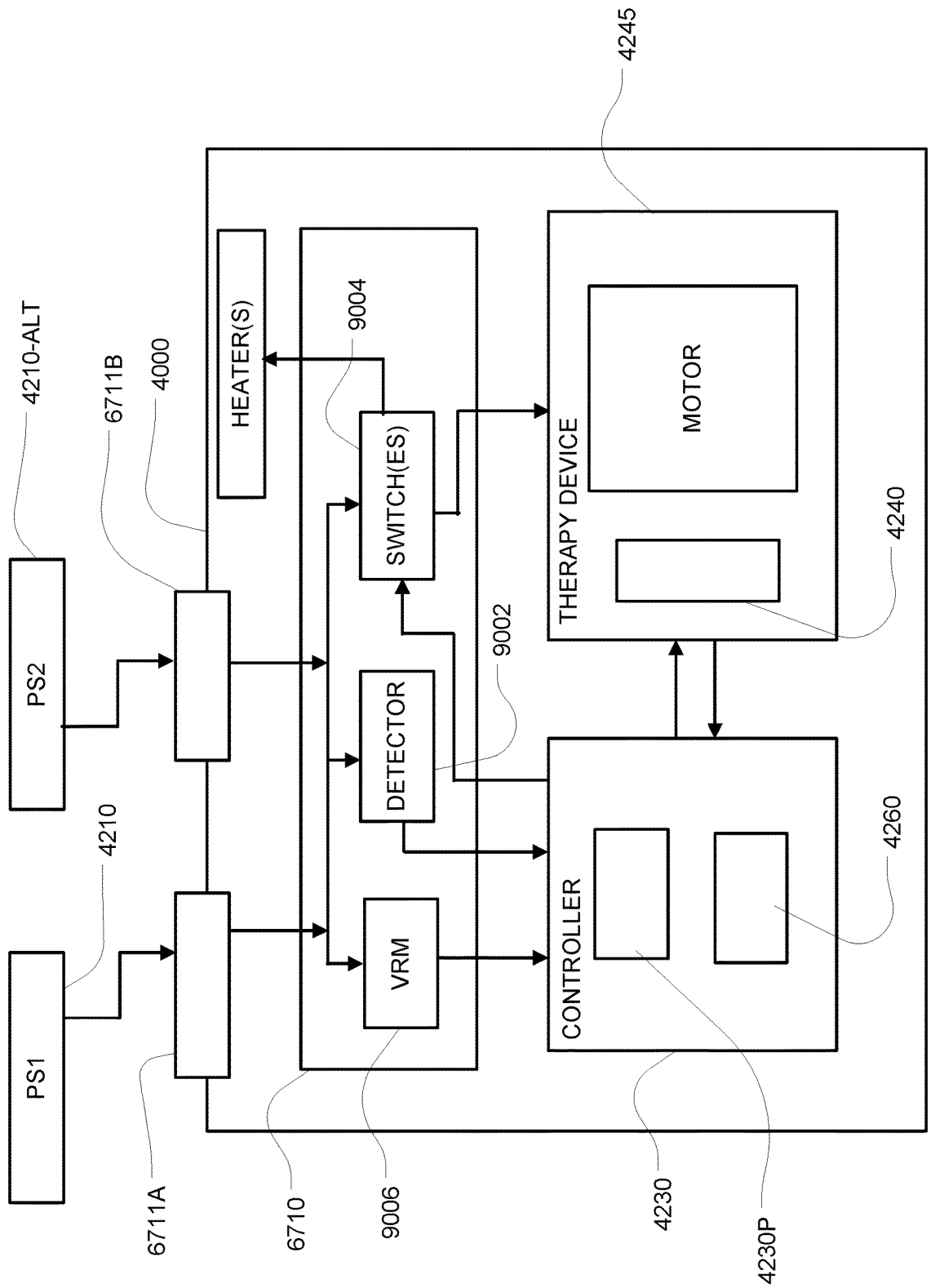
FIG. 9 is another schematic diagram of aspects of a RPT device showing a configuration of an input power circuit for different power supply operations in accordance with one aspect of the present technology.

As illustrated in FIG. 9, in some cases, the input power circuit 6710 may include one or more detection circuits. The detection circuit 9002 will typically be coupled to a controller in the RPT, such as the central controller 4230. The detection circuit 9002 may be configured to detect the type of power supply connected to the input power circuit. For example, in some cases, the input power circuit may include a voltage detector or voltage sensor circuit. Such a voltage detector/sensor may be configured to detect a voltage concerning, or unique to, the power supply that is coupled with the RPT. Thus, the voltage detector may detect an identification voltage or a supply voltage created by the coupled power supply. For example, in the case of the connection of an example 24-volt power supply (PS1), the voltage detector may detect a proportional voltage indicative of the 24-volt power supply and produce a signal indicative of such a voltage. A controller of the RPT, such as the central controller 4230 may receive the signal at an input port, such as a digital or analog input port, and determine from the signal that the high-power supply is connected. In the case of the connection of a 5-volt power supply (PS2), the voltage detector may detect a proportional voltage indicative of the 5-volt power supply and produce a signal indicative of such a voltage. A controller of the RPT, such as the central controller 4230 may receive the signal at the same or another input port, such as a digital or analog input port, and determine from the signal that the low power supply is connected.

In an example, the detector/sensor may be implemented with an operational amplifier configured as a comparator that compares a voltage or input voltage associated with the power supply to a suitable threshold voltage level chosen to differentiate the different power supplies (e.g., a 6-volt threshold or 7-volt threshold or other value etc.). The output signal from comparator may then be input to an input port of the controller or central controller 4230 to indicate the power supply. For example, a high (true) output signal from the comparator may indicate detection of a voltage greater than the threshold (e.g., a voltage greater than the low voltage of the low power supply such as the high-power supply voltage). Such a (high true) output signal may then be taken to indicate to the controller, such as at a digital input port of the controller, that the high-power power supply is connected. A low output signal from the comparator may indicate a voltage less than the threshold (e.g., a voltage lower than the high voltage of the high-power supply voltage). Such a low (false) signal, e.g. at the digital input port of the controller, may then be taken to indicate to the controller that the low-power power supply is connected. Other suitable comparisons with the comparator may also be implemented to produce a signal to the controller for such a determination.

In some versions, the voltage detector/sensor may produce a voltage proportional to the supplied voltage from the connected power supply (e.g., PS1 or PS2). Such a voltage may be sampled by a sampler or sampling circuit of the controller such as at an analog input port of the controller (e.g., the central controller 4230). The controller may then digitally compare the sampled value to one or more programmed thresholds of the controller to decide which power supply is connected.

In some versions, the input power circuit 6710 may also include one or more switching circuits 9004 for actively routing power based on detected type of power supply or detected power levels. Such switches may be coupled to one or more power/voltage rails of the RPT and a controller of the RPT. For example, based on the controller's detection of the connection of a particular power supply with the detection circuit, the controller may activate one or more switches to selectively permit power from the connected power supply via a voltage rail to supply current to a particular component or subset of components of the RPT. In this regard, an output signal from an output port of the controller, such as a digital output signal, may activate one or more transistors (e.g., semiconductor type transistor) to pass or activate power on rail(s) of the RPT from the power supply. For example, one or more of such switches may prevent connection of a supply line from the alternate power supply 4210-ALT (PS2) to therapy and/or heating devices of the RPT when the alternate power supply is connected to an interface 6711 of the RPT 4000. Similarly, such one or more of such switches may permit connection of a supply line from the power supply 4210 (PS1) to therapy and/or heating devices of the RPT when the power supply is connected to an interface 6711 of the RPT 4000.

In some cases, the input power circuit 6710 may include one or more voltage regulator module(s) 9006 or VRM, sometimes called PPM (processor power module) (e.g., a buck converter) that may power a controller of the RPT such as the central controller 4230. Such a voltage regulator module(s) may be coupled to receive supply power from either or both of the power supplies (PS1 and PS2) by the components and/or traces of the input power circuit. Such a voltage regulator module(s) may also be coupled to a controller and other low power components of the RPT. Thus, the voltage regulator may power the controller, e.g., central controller 4230, and optionally a communications circuit (e.g., data communications interface 4280), regardless of whether the power supply 4210 or the alternate power supply 4210-ALT is connected or coupled with the RPT 4000. Optionally, in some versions, such a voltage regulator module(s) may also power a display/display driver (e.g., output device 4290) and an input device 4220. Although not shown in the simplified version of FIG. 9 for purposes of illustrating the present technology, it is understood that additional circuit components may be included to effect powering of the one or more of the voltage regulators by either or both of the power supplies.

5.4.4 RPT Device Algorithms

As previously mentioned, the central controller may be implemented with algorithms in processes to implement the functions of a respiratory therapy device. Any one or more of the following example process modules may be included.

5.4.4.1 Mode of Operations Detection Module 4309

Figure 10:
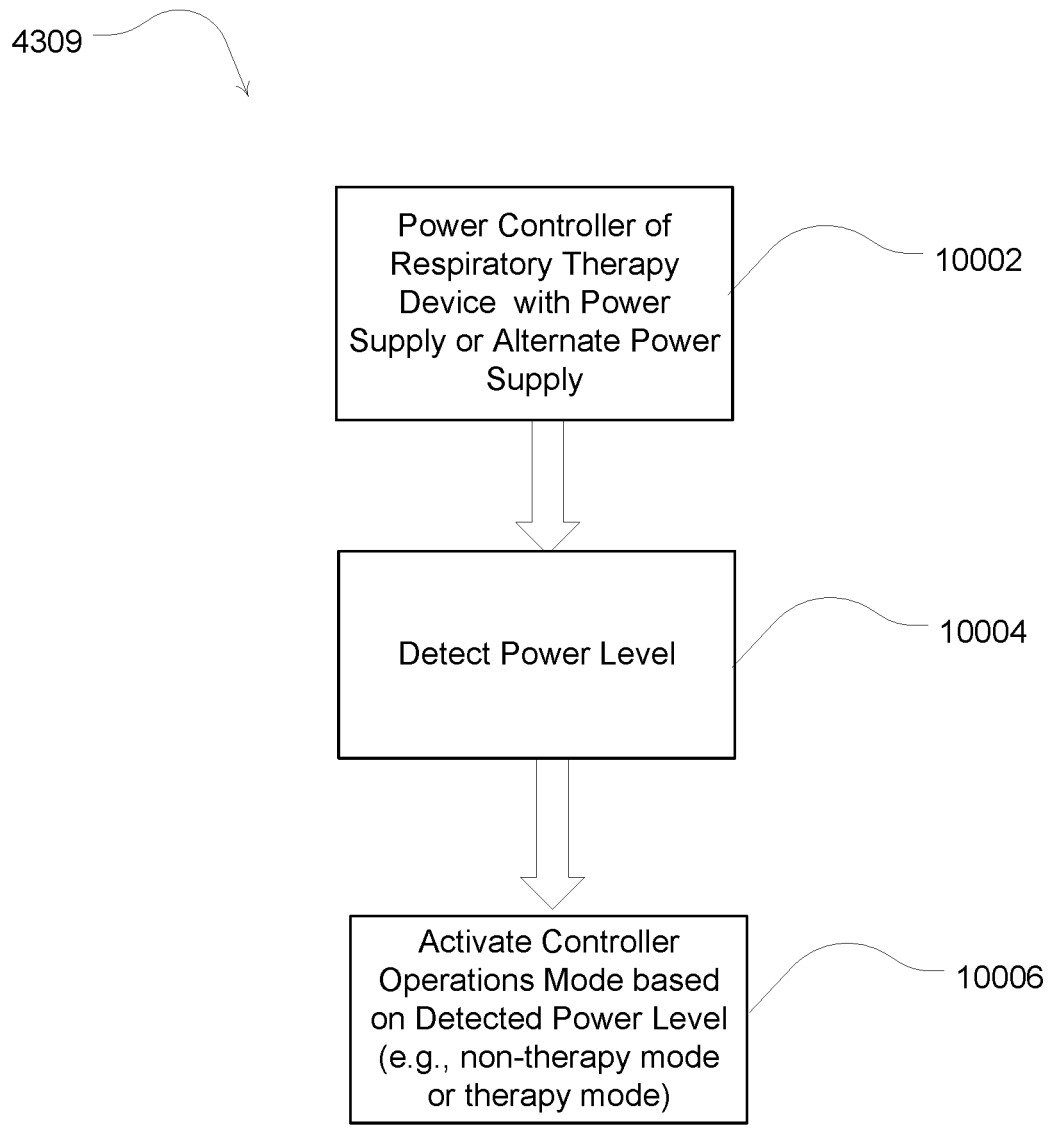
FIG. 10 is a flow diagram illustrating example mode selection methodology, such as for a controller, in some versions of the present technology.

As illustrated in reference to FIG. 10, a controller of the RPT, such as central controller 4230, may be configured to select between different operations modes depending on which of different power supplies (e.g., PS1 or PS2) are connected to the RPT. Such mode selections may be implemented by the controller in conjunction with the input power circuit 6710, including for example, its detection circuit 9002 as previously described. Such operations mode selections may be implemented to help users/healthcare equipment providers, with readily available power connections, to quickly and conveniently set up the respiratory device for the patient, to download data, to upload software, etc. in a 'low-power mode' that precludes therapy operations.

For example, a controller of the RPT device 4000, such as the central controller 4230, may implement the mode selection methodology illustrated in the flow chart of FIG. 10. In this regard, the controller may be initially powered on at 10002, such as with the connection of either power supply (PS1) or the alternate power supply (PS2). Optionally, a button may be provided on the RPT to activate (turn on) the RPT after connection of the power supply is made. As previously described, this may be powered by a voltage regulator module 9006 of the input power circuit 6710.

At 10004, the controller may then detect which power supply is connected to the RPT. For example, as previously described, the controller may detect the power supply (4210 or 4210-ALT), such as by detection of a power level type. Such a detection may be made by detection of a voltage with detection circuit 9002 (e.g., voltage detector/sensor). Such a detection may be based on a comparison between a predetermined reference voltage and a sensed voltage. Such a comparison may serve to identify that a high-power power supply is connected (e.g., a sufficient power supply for therapy operations) or a low-power power supply is connected (e.g., an insufficient power supply for therapy operations).

Thus, at 10006, the controller may activate a particular mode of operation based on the detection. For example, if a high-power power supply is detected, the controller may permit or run therapy operations, such as, the operations described in relation to the pre-processing module 4310 and the therapy Engine Module 4320 and control module 4330. Similarly, if a high-power power supply is detected the controller may activate therapy components such as the therapy device 4245 (e.g., a motor controller and motor of a blower) and/or heating controller and heating components such as for a humidifier 5000 and heated tube(s). Such activation may include activating one or more switches of switching circuits 9004 of the input power circuit 6710 for such components. To this end, the controller of the RPT may be configured to detect the available power from an external power source, and determine which of its subsystems to power on. The determination of which subsystem(s) to power on may be based on a predetermined hierarchy of subsystem priorities and the determined power output of the connected power supply.

If a low-power power supply is detected, the controller may permit or run non-therapy operations, such as, operations without use of particular high-power therapy components. In such low-power mode(s), the RPT device might only provide power on a first set of subsystems, such as its controller(s) and memory, and in some cases its display. In such mode(s), the controller(s) may operate merely for data access such as upload and download operations (e.g., parameter setting, software upgrades, diagnostic access). Such activation may include activating one or more switches of switching circuits 9004 of the input power circuit 6710 for such low-power components (e.g., a display or input device). Thus, an operation mode of a respiratory therapy device may be powered using a universal serial bus cable and universal serial bus power supply where the operation mode may involve accessing data or a memory of the respiratory therapy device. Alternatively, an operation mode of a respiratory therapy device may be powered using a wireless power transfer apparatus where the operation mode may involve accessing data or a memory of the respiratory therapy device.

For such low-power modes of operation, a user may then be able to change one or more settings on the RPT device or otherwise access data of the RPT device, such as using the on-board display or through an external device (e.g. tablet computer) that it is connected to the RPT device for data communications (either wired or wireless) with the RPT device 4000.

5.4.4.2 Pre-Processing Module 4310

With reference to FIG. 4D, once a therapy mode has been activated, for example, based on the mode of operations detections module, a pre-processing module 4310 in accordance with the present technology receives as an input, raw data from a transducer, for example a pressure transducer 4272 or a flow transducer 4274, and preferably performs one or more process steps to calculate one or more output values that will be used as an input to another module, for example a therapy engine module 4320.

In one form of the present technology, the output values include the interface or mask pressure Pm, the respiratory flow Qr, and the leak flow Ql.

In various forms of the present technology, the pre-processing module 4310 comprises one or more of the following algorithms: pressure compensation algorithm 4312, vent flow algorithm 4314, leak flow algorithm 4316, respiratory flow algorithm 4318, and jamming detection algorithm 4319.

5.4.4.2.1 Pressure Compensation

In one form of the present technology, a pressure compensation algorithm 4312 (shown in FIG. 4D) receives as an input a signal indicative of the pressure in the pneumatic path proximal to an outlet of the pneumatic block. The pressure compensation algorithm 4312 estimates the pressure drop in the air circuit 4170 and provides as an output an estimated pressure, Pm, in the patient interface 3000.

5.4.4.2.2 Vent Flow

In one form of the present technology, a vent flow algorithm 4314 (shown in FIG. 4D) for vent flow calculation receives as an input an estimated pressure, Pm, in the patient interface 3000 and estimates a vent flow of air, Qv, from a vent 3400 in a patient interface 3000.

5.4.4.2.3 Leak Flow

In one form of the present technology, a leak flow algorithm 4316 (shown in FIG. 4D) receives as an input a total flow, Qt, and a vent flow Qv, and provides as an output a leak flow Ql by calculating an average of Qt−Qv over a period sufficiently long to include several breathing cycles, e.g. about 10 seconds.

In one form, the leak flow algorithm 4316 receives as an input a total flow, Qt, a vent flow Qv, and an estimated pressure, Pm, in the patient interface 3000, and provides as an output a leak flow Ql by calculating a leak conductance, and determining a leak flow Ql to be a function of leak conductance and interface pressure, Pm. In one implementation, leak conductance is calculated as the quotient of low pass filtered non-vent flow Qt−Qv, and low pass filtered square root of mask pressure Pm, where the low pass filter time constant has a value sufficiently long to include several breathing cycles, e.g. about 10 seconds.

5.4.4.2.4 Respiratory Flow

In one form of the present technology, a respiratory flow algorithm 4318 receives as an input a total flow, Qt, a vent flow, Qv, and a leak flow, Ql, and estimates a respiratory flow to the patient, Qr, by subtracting the vent flow Qv and the leak flow Ql from the total flow Qt.

5.4.4.2.5 Jamming Detection

When the leak has recently changed and the leak flow algorithm 4316 has not fully compensated for the change, a state designated as "jamming" exists, which may be determined according to the methods described in U.S. Pat. Nos. 6,532,957, 6,810,876 or U.S. Patent Application Publication No. 2010/0101574 A1, the disclosures of which are incorporated herein by reference. In the jamming state, the respiratory flow baseline is usually incorrect to some degree, which distorts flow shapes and affects the detection of flow limitation. Jamming, which may be taken to represent an extent of uncompensated leak, is calculated by the jamming detection algorithm 4319 (shown in FIG. 4D).

5.4.4.3 Therapy Engine Module 4320

In one form of the present technology, a therapy engine module 4320 (shown in FIG. 4D) receives as inputs one or more of a pressure, Pm, in a patient interface 3000, a respiratory flow of air to a patient, Qr, a leak flow, Ql, a jamming variable and provides as an output, one or more therapy parameters.

In some versions of the present technology, a therapy parameter is a CPAP treatment pressure Pt or a bi-level pressure treatment.

In one form of the present technology, a therapy parameter is one or more of a level of pressure support, and a target ventilation.

5.4.4.3.1 Phase Determination

In one form of the present technology, the RPT device 4000 does not determine phase.

In one form of the present technology, a phase determination algorithm 4321 (shown in FIG. 4D) receives as an input a signal indicative of respiratory flow, Qr, and provides an estimate (D of the phase of a breathing cycle of the patient 1000. The rate of change of phase is indicative of the respiratory rate.

5.4.4.3.2 Waveform Determination

In one form of the present technology, a therapy control module 4330 controls a therapy device 4245 to provide an approximately constant positive airway pressure throughout a respiratory cycle of a patient.

In one form of the present technology, a therapy control module 4330 controls a therapy device 4245 to provide positive airway pressure according to a predetermined waveform of pressure versus phase. In one form, the waveform is maintained at an approximately constant level for all values of phase. In one form, the waveform is a square wave, having a higher value for some values of phase, and a lower level for other values of phase. In some cases, the therapy device may be controlled to provide a high flow therapy.

In one form of the present technology a waveform determination algorithm 4322 (shown in FIG. 4D) receives as an input a value indicative of current patient ventilation, Vent, and provides as an output a waveform of pressure vs. phase.

In one form, the waveform is a square wave, having a value of 1 for early values of phase corresponding to inspiration, and a value of 0 for later values of phase corresponding to expiration. In other forms, the waveform is a more "smooth and comfortable" waveform with a gradual rise to 1 for early values of phase, and a gradual fall to 0 for later values of phase.

5.4.4.3.3 Ventilation Determination

In one form of the present technology, a ventilation determination algorithm 4323 (shown in FIG. 4D) receives an input a respiratory flow Qr, and determines a measure indicative of patient ventilation, Vent.

In one form ventilation determination algorithm 4323 determines a current value of patient ventilation, Vent, as the half the low-pass filtered absolute value of respiratory flow, Qr.

5.4.4.3.4 Determination of Inspiratory Flow Limitation

In one form of the present technology, a processor executes one or more Inspiratory Flow limitation algorithms 4324 (shown in FIG. 4D) for the detection of inspiratory flow limitation.

In one form the inspiratory flow limitation algorithm 4324 receives as an input a respiratory flow signal Qr and provides as an output a metric of the extent to which the inspiratory portion of the breath exhibits inspiratory flow limitation.

The inspiratory flow limitation algorithm 4324 computes measures of at least one of the following three types of inspiratory flow limitation: ordinary flatness, M-shape, and "reverse chairness".

5.4.4.3.5 Detection of Apneas and Hypopneas

In one form of the present technology, a central controller 4230 executes one or more apneas and/or hypopneas algorithms 4325 (shown in FIG. 4D) for the detection of apneas and/or hypopneas.

5.4.4.3.6 Detection of Snore

In one form of the present technology, a central controller 4230 executes one or more snore algorithms 4326 (shown in FIG. 4D) for the detection of snore.

5.4.4.3.7 Determination of EPAP

In one form of the present technology, a number of different features indicative of upper airway obstruction ("UAO"), if present, cause a rise in the EPAP above a pre-set minimum value minimum EPAP, to a degree which is broadly proportional to the severity of the upper airway obstruction. When no features indicative of UAO are present, the EPAP decays progressively towards the pre-set minimum EPAP. This decay tends to minimise the EPAP delivered. At any given time, the EPAP is a balance between the forces tending to make it rise and the tendency to decay. An approximate equilibrium may be reached in which occasional indicators of mild UAO cause upward movements in EPAP which are counterbalanced by the decay that occurs when there are no indicators of UAO.

When the EPAP adjustment algorithm 4327 (shown in FIG. 4D) prescribes an increase in EPAP, that increase may not occur instantaneously. Such rises in EPAP may be controlled by the central controller 4230 and timed to occur only during what the RPT device 4000 considers to be inspiration. An example of such a technique is disclosed in U.S. Patent Application Publication No. 2011/0203588 A1, the disclosure of which is incorporated herein by reference.

5.4.4.3.8 Determination of Target Ventilation 4328

In some cases, a target ventilation may be set to a percentage (e.g., 90%) of the typical recent ventilation calculated as the output of a first-order low pass filter with time constant 3 minutes (the ventilation filter) that is applied to the instantaneous ventilation.

5.4.4.3.9 Determination of Therapy Parameters

The central controller 4230 executes one or more algorithms 4329 (shown in FIG. 4D) for the determination of therapy parameters.

5.4.4.4 Control Module 4330

A therapy control module 4330 in accordance with one form of the present technology receives as an input a target treatment pressure Pt, and controls a therapy device 4245 to deliver that pressure.

A therapy control module 4330 in accordance with another form of the present technology receives as inputs an EPAP, a waveform value, and a level of pressure support, computes a target treatment pressure Pt, and controls a therapy device 4245 to deliver that pressure.

A therapy control module 4330 in accordance with another form of the present technology receives as an input an EPAP, a waveform value, a target ventilation, and an instantaneous ventilation, computes a level of pressure support from the target ventilation and the instantaneous ventilation, computes a target treatment pressure Pt using the EPAP, the waveform value, and the pressure support, and controls a therapy device 4245 to deliver that pressure.

5.4.4.5 Detection of Fault Conditions

In one form of the present technology, a central controller 4230 may execute one or more methods for the detection of fault conditions. The fault conditions detected by the one or more methods may include at least one of the following:

Power failure (no power, or insufficient power)

Transducer fault detection

Failure to detect the presence of a component

Operating parameters outside recommended ranges (e.g. pressure, flow, temperature, $PaO_2$)

Failure of a test alarm to generate a detectable alarm signal.

Upon detection of the fault condition, the corresponding algorithm signals the presence of the fault by one or more of the following:

Initiation of an audible, visual and/or kinetic (e.g. vibrating) alarm

Sending a message to an external device

Logging of the incident

According to another aspect of the present technology, the central controller 4230 may omit a software module for detecting fault conditions. Rather, as discussed earlier, the detection of fault conditions may be handled exclusively by the fault mitigation integrated circuit that is separate from the central controller 4230. In some cases, the fault mitigation integrated circuit may serve as a redundant backup to similar fault detection/mitigation module with algorithms processed also within the central controller.

5.4.4.6 Therapy Device 4245

In a preferred form of the present technology, the therapy device 4245 (shown in FIG. 4C) is under the control of the therapy control module 4330 to deliver therapy to a patient 1000.

Preferably the therapy device 4245 is a positive air pressure device 4140.

5.5 Humidifier 5000

Figure 5:
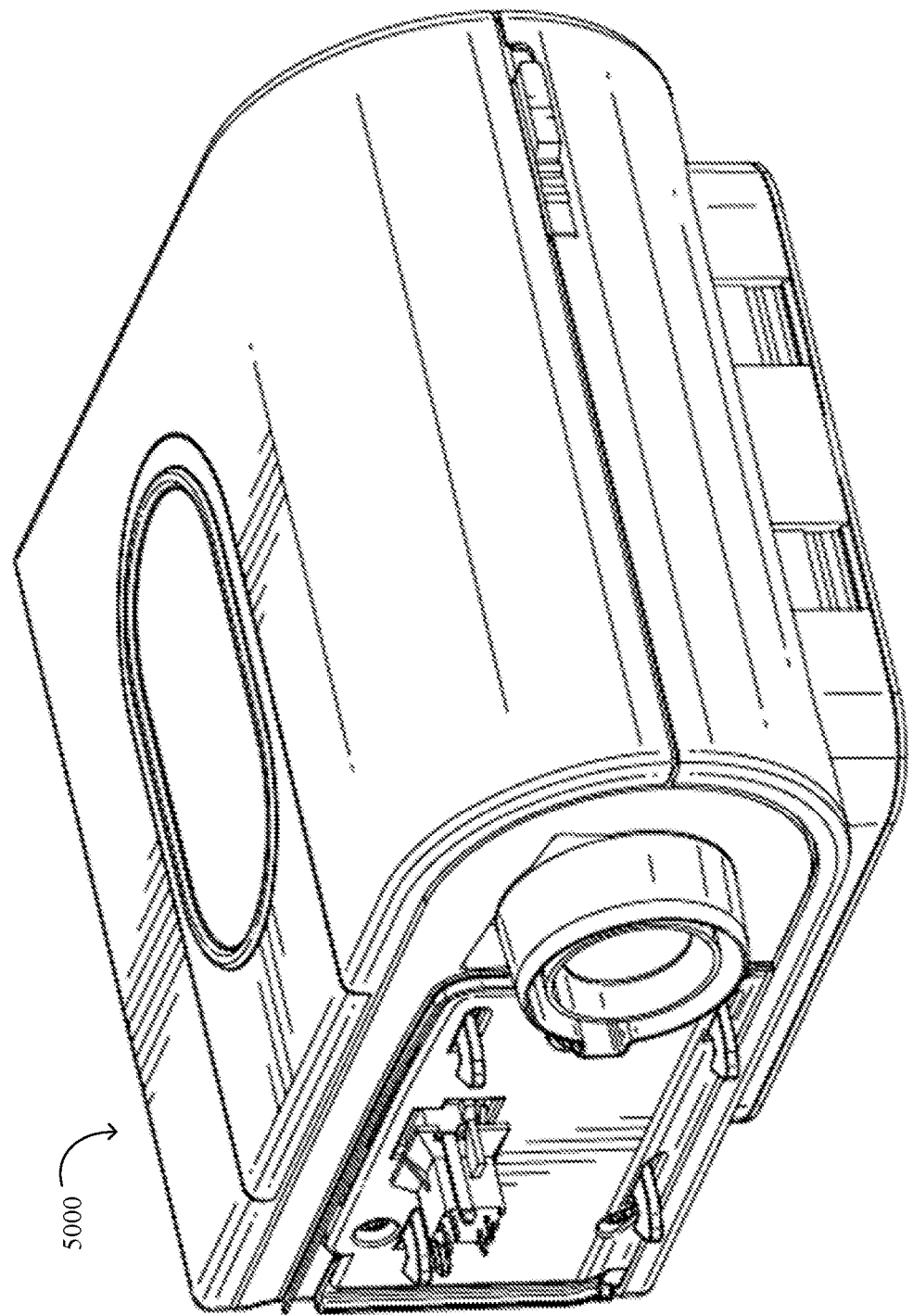
FIG. 5 shows a humidifier in accordance with one aspect of the present technology.
4.6 Example Power Control Components
Figure 6:
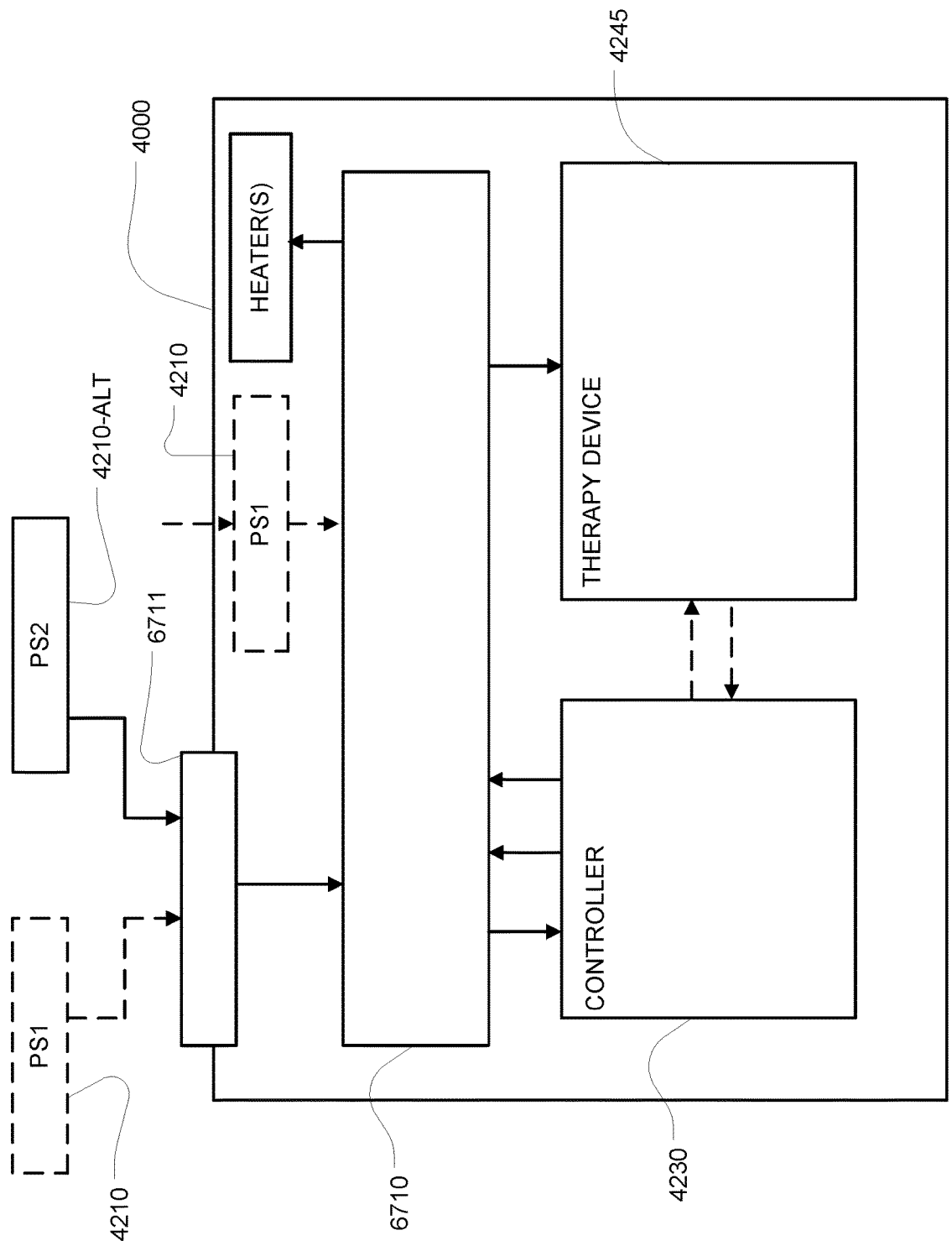
FIG. 6 is a schematic diagram of aspects of a RPT device showing a configuration with an input power circuit for different power supply operations using a common power input interface in accordance with one aspect of the present technology.

In one form of the present technology there is provided a humidifier 5000 (shown in FIG. 5) comprising a water reservoir and a heating plate.

Glossary

For the purposes of the present technology disclosure, in certain forms of the present technology, one or more of the following definitions may apply. In other forms of the present technology, alternative definitions may apply.

6.1 General

Air: In certain forms of the present technology, air supplied to a patient may be atmospheric air, and in other forms of the present technology atmospheric air may be supplemented with oxygen.

Continuous Positive Airway Pressure (CPAP): CPAP treatment will be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimetres of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

6.2 Aspects of RPT Devices

Air circuit: A conduit or tube constructed and arranged in use to deliver a supply of air or breathable gas between a RPT device and a patient interface. In particular, the air circuit may be in fluid connection with the outlet of the pneumatic block and the patient interface. The air circuit may be referred to as air delivery tube. In some cases there may be separate limbs of the circuit for inhalation and exhalation. In other cases a single limb is used.

APAP: Automatic Positive Airway Pressure. Positive airway pressure that is continually adjustable between minimum and maximum limits, depending on the presence or absence of indications of SDB events.

Blower or flow generator: A device that delivers a flow of air at a pressure above ambient pressure.

Controller: A device or portion of a device that adjusts an output based on an input. For example, one form of controller has a variable that is under control—the control variable—that constitutes the input to the device. The output of the device is a function of the current value of the control variable, and a set point for the variable. A servo-ventilator may include a controller that has ventilation as an input, a target ventilation as the set point, and level of pressure support as an output. Other forms of input may be one or more of oxygen saturation (SaO2), partial pressure of carbon dioxide (PCO2), movement, a signal from a photoplethysmogram, and peak flow. The set point of the controller may be one or more of fixed, variable or learned. For example, the set point in a ventilator may be a long term average of the measured ventilation of a patient. Another ventilator may have a ventilation set point that changes with time. A pressure controller may be configured to control a blower or pump to deliver air at a particular pressure. A controller may include or be a microcontroller, microprocessor or processor.

Therapy: Therapy in the present context may be one or more of positive pressure therapy, high flow therapy, oxygen therapy, carbon dioxide therapy, control of dead space, and the administration of a drug.

Motor: A device for converting electrical energy into rotary movement of a member. In the present context the rotating member is an impeller, which rotates in place around a fixed axis so as to impart a pressure increase to air moving along the axis of rotation.

Positive Airway Pressure (PAP) device: A device for providing a supply of air at positive pressure to the airways.

Transducers: A device for converting one form of energy or signal into another. A transducer may be a sensor or detector for converting mechanical energy (such as movement) into an electrical signal. Examples of transducers include pressure sensors, flow sensors, carbon dioxide ($CO_2$) sensors, oxygen ($O_2$) sensors, effort sensors, movement sensors, noise sensors, a plethysmograph, and cameras.

Volute: The casing of the centrifugal pump that receives the air being pumped by the impeller, slowing down the flow rate of air and increasing the pressure. The cross-section of the volute increases in area towards the discharge port.

6.3 Aspects of the Respiratory Cycle

Apnea: An apnea will be said to have occurred when flow falls below a predetermined threshold for a period of duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort.

Breathing rate: The rate of spontaneous respiration of a patient, usually measured in breaths per minute.

Duty cycle: The ratio of inhalation time, Ti to total breath time, Ttot.

Effort (breathing): Preferably breathing effort will be said to be the work done by a spontaneously breathing person attempting to breathe.

Expiratory portion of a breathing cycle: The period from the start of expiratory flow to the start of inspiratory flow.

Flow limitation: Preferably, flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
(i) Flattened: Having a rise followed by a relatively flat portion, followed by a fall.
(ii) M-shaped: Having two local peaks, one at the leading edge, and one at the trailing edge, and a relatively flat portion between the two peaks.
(iii) Chair-shaped: Having a single local peak, the peak being at the leading edge, followed by a relatively flat portion.
(iv) Reverse-chair shaped: Having a relatively flat portion followed by single local peak, the peak being at the trailing edge.

Hypopnea: Preferably, a hypopnea will be taken to be a reduction in flow, but not a cessation of flow. In one form, a hypopnea may be said to have occurred when there is a reduction in flow below a threshold for a period of duration. In one form in adults, the following either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Inspiratory portion of a breathing cycle: Preferably the period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed.

Positive End-Expiratory Pressure (PEEP): The pressure above atmosphere in the lungs that exists at the end of expiration.

Peak flow (Qpeak): The maximum value of flow during the inspiratory portion of the respiratory flow waveform.

Respiratory flow, airflow, patient airflow, respiratory airflow (Qr): These synonymous terms may be understood to refer to the RPT device's estimate of respiratory airflow, as opposed to "true respiratory flow" or "true respiratory airflow", which is the actual respiratory flow experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow waveform.

(exhalation) Time (Te): The duration of the expiratory portion of the respiratory flow waveform.

(total) Time (Ttot): The total duration between the start of the inspiratory portion of one respiratory flow waveform and the start of the inspiratory portion of the following respiratory flow waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system, including both inspiratory and expiratory flow, per unit time. When expressed as a volume per minute, this quantity is often referred to as "minute ventilation". Minute ventilation is sometimes given simply as a volume, understood to be the volume per minute.

6.4 RPT Device Parameters

Flow rate: The instantaneous volume (or mass) of air delivered per unit time. While flow rate and ventilation have the same dimensions of volume or mass per unit time, flow rate is measured over a much shorter period of time. Flow may be nominally positive for the inspiratory portion of a breathing cycle of a patient, and hence negative for the expiratory portion of the breathing cycle of a patient. In some cases, a reference to flow rate will be a reference to a scalar quantity, namely a quantity having magnitude only. In other cases, a reference to flow rate will be a reference to a vector quantity, namely a quantity having both magnitude and direction. Flow will be given the symbol Q. Total flow, Qt, is the flow of air leaving the RPT device. Vent flow, Qv, is the flow of air leaving a vent to allow washout of exhaled gases. Leak flow, Ql, is the flow rate of unintentional leak from a patient interface system. Respiratory flow, Qr, is the flow of air that is received into the patient's respiratory system.

Leak: Preferably, the word leak will be taken to be a flow of air to the ambient. Leak may be intentional, for example to allow for the washout of exhaled $CO_2$. Leak may be unintentional, for example, as the result of an incomplete seal between a mask and a patient's face.

Pressure: Force per unit area. Pressure may be measured in a range of units, including $cmH_2O$, $g-f/cm^2$, and hectopascal. $1 cmH_2O$ is equal to $1 g-f/cm^2$ and is approximately 0.98 hectopascal. In this specification, unless otherwise stated, pressure is given in units of $cmH_2O$. For nasal CPAP treatment of OSA, a reference to treatment pressure is a reference to a pressure in the range of about 4-20 $cmH_2O$, or about 4-30 $cmH_2O$. The pressure in the patient interface is given the symbol Pm.

Sound Power: The energy per unit time carried by a sound wave. The sound power is proportional to the square of sound pressure multiplied by the area of the wavefront. Sound power is usually given in decibels SWL, that is, decibels relative to a reference power, normally taken as $10^{-12}$ watt.

Sound Pressure: The local deviation from ambient pressure at a given time instant as a result of a sound wave travelling through a medium. Sound power is usually given in decibels SPL, that is, decibels relative to a reference power, normally taken as $20 \times 10^{-6}$ Pascal (Pa), considered the threshold of human hearing.

6.5 Terms for Ventilators

Adaptive Servo-Ventilator: A ventilator that has a changeable, rather than fixed target ventilation. The changeable target ventilation may be learned from some characteristic of the patient, for example, a respiratory characteristic of the patient.

Backup rate: A parameter of a ventilator that establishes the minimum respiration rate (typically in number of breaths per minute) that the ventilator will deliver to the patient, if not otherwise triggered.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

EPAP (or EEP): a base pressure, to which a pressure varying within the breath is added to produce the desired mask pressure which the ventilator will attempt to achieve at a given time.

IPAP: desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the minimum value during expiration (e.g., PS=IPAP−EPAP). In some contexts pressure support means the difference which the ventilator aims to achieve, rather than what it actually achieves.

Servo-ventilator: A ventilator that measures patient ventilation has a target ventilation, and which adjusts the level of pressure support to bring the patient ventilation towards the target ventilation.

Spontaneous/Timed (SIT)—A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Ventilator: A mechanical device that provides pressure support to a patient to perform some or all of the work of breathing.

Ventilator inspiration and ventilator expiration: the periods during which the ventilator considers that it should deliver pressures appropriate respectively to patient inspiration and expiration. Depending on the quality of patient-ventilator synchronisation, and the presence of upper airway obstruction, these may or may not correspond to actual patient inspiration or expiration.

6.6 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

OTHER REMARKS

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

The invention claimed is:

1. A method for a respiratory therapy device comprising powering an operational mode of a respiratory therapy device using a universal serial bus cable and universal serial bus power supply, the operational mode comprising accessing and/or downloading data of the respiratory therapy device using an external universal serial bus power provided to the respiratory therapy device with the universal serial bus cable, and routed to power only a subset of power components of the respiratory therapy device, and using an on-board display of the respiratory therapy device or either wired or wireless communications with the respiratory therapy device.

2. The method of claim 1, wherein the universal serial bus power supply is a low-power power supply.

3. The method of claim 1, wherein the operational mode is a non-therapy operational mode.

4. The method of claim 1, wherein the respiratory therapy device comprises a blower configured to operate in a therapy mode with a power source other than the universal serial bus power supply.

5. The method of claim 4, wherein the power source other than the universal serial bus power supply is a mains power source.

6. The method of claim 5, wherein a therapy provided by the therapy mode comprises a positive pressure therapy to an airway of a patient.

7. The method of claim 4, wherein a therapy provided by the therapy mode comprises a high flow therapy to an airway of a patient.

8. A respiratory therapy apparatus configured to be powered in an operation mode by a universal serial bus cable and universal serial bus power supply, the operation mode comprising access to, and/or downloading of data from, a memory of the respiratory therapy apparatus, wherein the respiratory therapy apparatus is configured to use an external universal serial bus power provided to the respiratory therapy apparatus with the universal serial bus cable, wherein the respiratory therapy apparatus is configured to route the power to only a subset of power components of the respiratory therapy apparatus, and configured to perform the operation mode using an on-board display of the respiratory therapy apparatus or either wired or wireless communications with the respiratory therapy apparatus.

9. The respiratory therapy apparatus of claim 8, wherein the universal serial bus power supply is a low-power power supply and the respiratory therapy apparatus comprises an external interface for coupling with the universal serial bus cable that couples with the universal serial bus power supply.

10. The respiratory therapy apparatus of claim 8, wherein the operation mode is a non-therapy operation mode.

11. The respiratory therapy apparatus of claim 8, wherein the respiratory therapy apparatus comprises a blower configured to operate in a therapy mode with a power source other than the universal serial bus power supply.

12. The respiratory therapy apparatus of claim 11, wherein the power source other than the universal serial bus power supply is a mains power source.

13. The respiratory therapy apparatus of claim 12, wherein a therapy provided by the therapy mode comprises a positive pressure therapy to an airway of a patient.

14. The respiratory therapy apparatus of claim 12, wherein a therapy provided by the therapy mode comprises a high flow therapy to an airway of a patient.

* * * * *